(12) United States Patent
Lee

(10) Patent No.: US 7,888,507 B2
(45) Date of Patent: *Feb. 15, 2011

(54) UV EXCITABLE FLUORESCENT ENERGY TRANSFER DYES

(76) Inventor: Linda G. Lee, 2680 Ramona St., Palo Alto, CA (US) 94306

( * ) Notice: Subject to any disclaimer, the term of this patent is extended or adjusted under 35 U.S.C. 154(b) by 0 days.

This patent is subject to a terminal disclaimer.

(21) Appl. No.: 12/126,813

(22) Filed: May 23, 2008

(65) Prior Publication Data

US 2009/0031506 A1 Feb. 5, 2009

Related U.S. Application Data

(60) Continuation of application No. 11/497,159, filed on Jul. 31, 2006, now Pat. No. 7,378,517, which is a continuation of application No. 10/359,826, filed on Feb. 7, 2003, now Pat. No. 7,157,572, which is a continuation of application No. 09/902,562, filed on Jul. 10, 2001, now abandoned, which is a division of application No. 09/385,352, filed on Aug. 27, 1999, now Pat. No. 6,358,684.

(51) Int. Cl.
*C07D 213/00* (2006.01)
*C07D 215/00* (2006.01)
*C07D 471/00* (2006.01)
*C07D 263/62* (2006.01)
*C12Q 1/68* (2006.01)

(52) U.S. Cl. ............................ 546/1; 546/16; 546/34; 548/219; 435/6

(58) Field of Classification Search .................... 435/6; 546/1, 16, 34; 548/219
See application file for complete search history.

(56) References Cited

U.S. PATENT DOCUMENTS

| | | | |
|---|---|---|---|
| 4,777,128 A | 10/1988 | Lippa | |
| 4,996,143 A | 2/1991 | Heller et al. | |
| 5,118,802 A | 6/1992 | Smith et al. | |
| 5,188,934 A | 2/1993 | Menchen et al. | |
| 5,254,477 A | 10/1993 | Walt | |

(Continued)

FOREIGN PATENT DOCUMENTS

EP    0 201 751 A2    11/1986

(Continued)

OTHER PUBLICATIONS

U.S. Appl. No. 11/617,650, filed Dec. 28, 2006, Lee et al.

(Continued)

*Primary Examiner*—Jezia Riley

(57) ABSTRACT

Novel energy transfer dyes which can be used with shorter wavelength light sources are provided. These dyes include a donor dye with an absorption maxima at a wavelength between about 250 to 450 nm and an acceptor dye which is capable of absorbing energy emitted from the donor dye. One of the energy transfer dyes has a donor dye which is a member of a class of dyes having a coumarin or pyrene ring structure and an acceptor dye which is capable of absorbing energy emitted from the donor dye, wherein the donor dye has an absorption maxima between about 250 and 450 nm and the acceptor dye has an emission maxima at a wavelength greater than about 500 nm.

1 Claim, 15 Drawing Sheets

U.S. PATENT DOCUMENTS

| | | | |
|---|---|---|---|
| 5,326,692 | A | 7/1994 | Brinkley et al. |
| 5,340,716 | A | 8/1994 | Ullman et al. |
| 5,342,789 | A | 8/1994 | Chick et al. |
| 5,401,847 | A | 3/1995 | Glazer et al. |
| 5,410,030 | A | 4/1995 | Yue et al. |
| 5,439,797 | A | 8/1995 | Tsien et al. |
| 5,532,129 | A | 7/1996 | Heller |
| 5,552,540 | A | 9/1996 | Haralambidis |
| 5,565,322 | A | 10/1996 | Heller |
| 5,565,554 | A | 10/1996 | Glazer et al. |
| 5,573,909 | A | 11/1996 | Singer et al. |
| 5,582,977 | A | 12/1996 | Yue et al. |
| 5,607,834 | A | 3/1997 | Bagwell |
| 5,646,264 | A | 7/1997 | Glazer et al. |
| 5,654,419 | A | 8/1997 | Mathies et al. |
| 5,688,648 | A | 11/1997 | Mathies et al. |
| 5,707,804 | A | 1/1998 | Mathies et al. |
| 5,728,528 | A | 3/1998 | Mathies et al. |
| 5,760,201 | A | 6/1998 | Glazer et al. |
| 5,763,189 | A | 6/1998 | Buechler et al. |
| 5,800,996 | A * | 9/1998 | Lee et al. ............ 435/6 |
| 5,824,799 | A | 10/1998 | Buechler et al. |
| 5,843,658 | A | 12/1998 | Uchiyama et al. |
| 5,851,778 | A | 12/1998 | Oh et al. |
| 5,853,992 | A | 12/1998 | Glazer et al. |
| 5,863,727 | A * | 1/1999 | Lee et al. ............ 435/6 |
| 5,869,255 | A | 2/1999 | Mathies et al. |
| 5,945,283 | A | 8/1999 | Kwok et al. |
| 5,945,526 | A * | 8/1999 | Lee et al. ............ 536/26.6 |
| 5,981,200 | A | 11/1999 | Tsien et al. |
| 6,008,373 | A | 12/1999 | Waggoner et al. |
| 6,028,190 | A | 2/2000 | Mathies et al. |
| 6,048,982 | A | 4/2000 | Waggoner |
| 6,218,124 | B1 | 4/2001 | Lee |
| 6,358,684 | B1 | 3/2002 | Lee et al. |
| 6,482,938 | B1 | 11/2002 | Hayashizaki et al. |
| 6,849,745 | B2 * | 2/2005 | Lee et al. ............ 549/223 |
| 7,012,141 | B2 | 3/2006 | Lee |
| 7,157,572 | B2 | 1/2007 | Lee |
| 7,169,939 | B2 | 1/2007 | Lee et al. |
| 2004/0076971 | A1 | 4/2004 | Lee et al. |
| 2007/0154924 | A1 | 7/2007 | Lee et al. |
| 2007/0154925 | A1 | 7/2007 | Lee et al. |
| 2007/0154926 | A1 | 7/2007 | Lee et al. |
| 2007/0154927 | A1 | 7/2007 | Lee et al. |
| 2007/0161026 | A1 | 7/2007 | Lee et al. |
| 2007/0161027 | A1 | 7/2007 | Lee et al. |
| 2007/0207477 | A1 | 9/2007 | Lee et al. |
| 2007/0212709 | A1 | 9/2007 | Lee et al. |

FOREIGN PATENT DOCUMENTS

| | | |
|---|---|---|
| EP | 0 229 943 A2 | 7/1987 |
| EP | 0 299 943 B1 | 7/1987 |
| EP | 0 601 889 A2 | 6/1994 |
| EP | 0 747 700 A2 | 12/1996 |
| EP | 0 967 219 A1 | 12/1999 |
| GB | 2301833 A | 12/1996 |
| JP | 5-60698 | 3/1993 |
| WO | WO 89/03041 A2 | 4/1989 |
| WO | WO 89/03041 A3 | 4/1989 |
| WO | WO 92/00388 | 1/1992 |
| WO | WO 93/06482 | 4/1993 |
| WO | WO 93/09128 | 5/1993 |
| WO | WO 93/13224 | 7/1993 |
| WO | WO 93/23492 | 11/1993 |
| WO | WO 94/17397 | 8/1994 |
| WO | WO 94/28166 | 12/1994 |
| WO | WO 95/21266 | 8/1995 |
| WO | WO 96/04405 | 2/1996 |
| WO | WO 96/30540 | 10/1996 |
| WO | WO 96/41166 | 12/1996 |
| WO | WO 97/11084 | 3/1997 |
| WO | WO 99/02544 | 1/1999 |
| WO | WO 01/16369 A2 | 3/2001 |

OTHER PUBLICATIONS

U.S. Appl. No. 11/618,667, filed Dec. 29, 2006, Lee et al.

Abdel-Mottaleb, M.S.A., et al., "Photophysics and dynamics of coumarin laser dyes and their analytical implications", *Proc.-Indian Acad. Scie. Chem. Sci.*, 1992, 104: 185-196.

Anton, J.A., et al., "Transfer of Excitation Energy Between Porphyrin Centers of a Covalently-Linked Dimer", *Photochemistry and Photobiology*, 1978, 28: 235-242.

Asseline, U., et al., "Oligonucleotides Covalently Linked to Intercalating Dyes as Base Sequence-Specific Ligands: Influence of Dye Attachment Site", *EMBO Journal*, 1984, 3: 795-800.

Benson, S., et al., "Fluorescence Energy-Transfer Cyanine Heterodimers with High Affinity for Double-Stranded DNA-I. Synthesis and Spectroscopic Properties", *Analytical Biochemistry*, Jun. 1995, pp. 247-255.

Benson, S.C., et al., "Heterodimeric DNA-binding dyes designed for energy transfer: stability and applications of the DNA complexes", *Nucleic Acid Research*, Nov. 1993, 21: 5720-5726.

Benson, S.C., et al.' "Heterodimeric DNA-binding dyes designed for energy transfer: synthesis and spectroscopic properties", *Nucleic Acids Research*, Nov. 1993, 21: 5727-5735.

Bergstrom, D., et al., "C-5-substituted Nucleoside Analogs", *SYNLETT*, 1992, 3: 179-188.

Bothner, A.A., et al., "Molecular Dynamics of covalently linked multi-porphyrin arrays", *J. Phys. Chem.*, 1996, 100: 17551-17557.

Brumbaugh, J., et al., "Continuous On-Line DNA Sequencing Using Oligonucleotide Primers with Multiple Fluorophores", *Proc. Natl. Acad. Sci. USA*, 1988, 85: 5610-5614.

Cardullo, R.A., et al., "Detection of nucleic acid hybridization by nonradiative fluorescence resonance energy transfer", *Proc. Natl. Acad. Sci. USA*, Dec. 1988, 85(23): 8790-8794.

Chiu, H.C., et al., "Electronic energy transfer between tyrosine and tryptophan in the peptides Tyr-(Pro)n-Tyr", *Biopolymers*, 1977, 16: 277.

Clegg, R.M., "Fluorescence resonance energy transfer and nucleic acids", *Method Enzymol.*, 1992, 211: 353-388.

Conrad, R.H., et al., "Intramolecular transfer of excitation from tryptophan to 1-dimethylaminonaphthalene-5-sulfonamide in a series of model compounds", *Biochemistry*, 1968, 7: 777.

Cooper, J., et al., "Analysis of Fluorescence Energy Transfer in Duplex and Branched DNA Molecules", *Biochemistry*, 1990, 29(39): 9261-9268.

Delaney, J.K., et al., "Electron tunneling in a cofacial zinc porphyrin-quinone cage molecule: Novel Temperature and solvent dependent", *J. Am. Chem. Soc.*, 1990, 112(3): 957-963.

Dirks, G., et al., "Light absorption and energy transfer in polyene-porphyrin esters", *Photochemistry and Photobiology*, 1980, 32: 277-280.

Drake, J.M., et al., "Chemical and Biological Microstructures as Probed by Dynamic Processes", *Science*, Mar. 1991, 251: 1574-1579.

Effenberger, F., et al., "Synthesis and optical properties of terminally substituted conjugated polyenes", *Agnew. Chem. Int. Ed. Engl.*, 1988, 27(2): 281-284.

Florkin, M., et al., "Mechanism of energy transfer", *Comprehensive Biochemistry*, 1967, 22: 61.

Forster, T., "Intermolecular Energy Migration and fluorescence", *Ann. Physik (Leipzig)*, 1948, 2: 55.

Gust, D., et al., "A synthetic system mimicking the energy transfer and charge separation of natural photosynthesis", *Journal of Photochemistry*, 1985, 27(2): 281-284.

Ha, T., et al., "Probing the Interaction between two single molecules: Fluorescence resonance energy transfer between a single donor and a single acceptor", *Biophysics*, Jun. 1996, 93: 6264-6268.

Haralambidis, J., et al., "Preparation of base-modified nucleosides suitable for non-radioactive label attachment and their incorporation into synthetic oligodeoxyribonucleotides", *Nucleic Acids Research*, 1987, 15(12): 4857-4876.

Hass, E., et al., "Distribution of end to end Distances in oligopeptides in solution as estimated by energy transfer", *Proc. Natl. Acad. Sci. USA*, 1975, 72: 1807.

Haugland, R.P., "Fluorescence-Detected DNA Sequencing—Final Technical Report", Grant No. DE-FG06-88ER60684, Sep. 1990, 15 pages.

Haugland, R.P., "Fluorescent Labels", *Biosense. Fiberopt.*, 1991, 85-110.

Haugland, R.P., "Synthesis and applications of fluorescent probes", *Small Business Innovative Research Program, Phase II Grant Application*, 1988.

Haugland, R.P., "Synthesis and Biomedical Applications of Fluorescent Probes", *Small Business Innovative Research Program, Phase I Grant Application*, Dec. 1985.

Haugland, R.P., et al., "Dependence of the Kinetics of singlet-singlet energy transfer on spectral overlap", *Proc. Natl. Acad. Sci.*, 1969, 63: 23-30.

Haugland, R.P., et al., "New Dyes for DNA Sequencing" (Progress Report) Dec. 31, 1990.

Heller, M.J., et al., "Fluorescent energy transfer oligonucleotide probes", *Federation Proceedings*, 1987, 46(6) Abstract 248.

Ozaki, Hiroaki, et al., "Fluorescence resonance energy transfer between specific-labeled sites on DNA", 1992, pp. 67-68.

Ozaki, Hiroaki, et al., "The Estimation of Distances Between Specific Backbone-Labeled Sites in DNA using Flurorescence Resonance Energy Transfer", *Nucleic Acids Research*, Sep. 1992, pp. 5205-5214.

Hirzel, T.K., "Singlet excitation transfer between terminal chromophores in 1,4-disubstituted bicyclo (2.2.2.) octanes and 4,4'-disubstituted —1,1'dibicyclo (2.2.2) octyls", Ph.D. Dissertation 1980, University of Wisconsin-Madision.

Hsiao, J.S., et al., "Soluble synthetic multiporphyrin arrays. Photodynamics of energy-transfer processes", *J. Am. Chem. Soc.*, 1996, 118(45): 11181-11193.

Hung, S., et al., "Cyanine Dyes with High Absorption Cross Section as Donor Chromophores in Energy Transfer Primers", *Anal. Biochem.*, 1996, 243: 15-27.

Hung, S.C., et al., "Cyanine Dyes With High Absorption Cross Section as Donor Chromophores in Energy Transfer Primers", *Anal. Biochem.*, 1996, 243: 15-27.

Hung, S.C., et al., "Energy Transfer Primers with 5- or 6-carboxyrhodamine-6G a acceptor chromophores", *Anal. Biochem.*, 1996, 238: 165-170.

Hwang, K.C., et al "Synthesis of Amphipathic porphyrings and their photoinduced electron transfer reactions at the lipid bilayer-water interface", *Photochemistry and Photobiology*, 1994, 59: 145-151.

Ju, J., et al., "Cassette Labeling for facile construction of energy transfer fluorescent primers", *Nucleic Acid Res.*, 1996, 24: 1144-1148.

Ju, J., et al., "Design and synthesis of fluorescence energy transfer dye-labeled primers and their application for DNA sequencing and analysis", *Anal. Biochem.*, Oct. 10, 1995, 231(1): 131-140.

Ju, J., et al., "Fluorescence energy transfer dye-labeled primers for DNA sequencing and analysis", Proc. Nat'l Acad. Sci. WA, Jan. 1995, pp. 4347-4350.

Kang, H-C, et al., "New Dyes for DNA sequencing", *Human Genome 1989-90, Program report (U.S. Department of Energy, Office of Energy)*.

Katz, H.E., et al., "4-Piperidinylimino: A Nearly Linear Head-to-Tail linking Group for Dipolar Chrmophores", *Journal of Organic Chemistry*, 1991, 56: 2282-2284.

Lamola, A.A. et al., "Intramolecular energy transfer between nonconjugated chromophores in some model compounds", *J. Am. Chem. Soc.*, 1965, 37:2322.

Latt, S.A., et al., "Energy transfer. A systems with relatively fixed donor-acceptor separation", *J. Am. Chem. Soc.*, 1965, 87: 995-1003.

Lee et al., "DNA sequencing with dye-labeled terminators and T7 DNA polymerase: effect of dyes and dNTPs on incorporation of dye-terminators and probability analysis of termination fragments," *Nucleic Acids Res.*, 1992, 20(10): 2471-2483.

Lee, L.G., et al., "Allelic discrimination by nick-translation PCR with fluorogenic probes", *Nucleic Acids Res.*, Aug. 11, 1993, 21(16): 3761-3766.

Lerho, M.J., "Diffusion-enhanced fluorescence energy transfer (DEFET): Application to the study of ligands-DNA and chromatin interaction", Ph.D. Dissertation 1991, University of Belgium.

Lindsey, J.S., et al., "Excited-state porphyrin-quinone interactions at 10-A separation", *J. Am. Chem. Soc.*, 1982, 104(16): 4498-4500.

Lindsey, J.S., et al., "Photophysics of a cofacial porphyrin-quinone cage molecule and related compounds: Fluorescence properties, flash transients, and electron-transfer reactions", *J. Am. Chem. Soc.*, 1988, 110(11): 3610-3621.

Lindsey, J.S., et al., "Synthesis of a cofacial porphyrin-quinone via entropically favored macropolycyclization", *J. Am. Chem. Soc.*, Aug. 11, 1982, 104(16): 4498-4500.

Lindsey, J.S., et al., "Visible light-harvesting in covalently-linked porphyrin-cyanine dyes", *Tetrahedron*, 1989, 45(15): 4845-4866.

Livak, K.J., et al., "Oligonucleotides with fluorescent dyes at opposite ends provide a quenched probe system useful for detecting PCR product and nucleic acid hybridization", *PCR Method Appl.*, Jun. 1995, 4(6): 357-362.

Mergny, J., et al., "Fluorescence energy transfer as a probe for nucleic acid structures and sequences", *Nucleic Acids Research*, Feb. 1994, 22: 920-928.

Millarar, D.P., et al., "Excited-state quenching of dye-linked oligonucleotides", *Proc. Spie-Int. Soc. Opt. Engl.*, 1992, 1640: 592-598.

Mitsui et al., "Courmarin-fluorescein pair as a new donor-acceptor set for fluorescence energy transfer study of DNA," *Tetrahedron Letters*, Apr. 2000, 41:2605-2608.

Moore, A.L., et al., "Energy transfer from carontenoid polyenes to porphyrins: A light harbesting antenna", *Photochemistry and Photobiology*, 1980, 32: 691-695.

Mugnier, J., et al., "Efficiency of intramolecular energy transfer in coumarin bichromophoric molecules", *J. Lumin.*, 1985, 33: 273.

Mugnier, J., et al., "Rate of intramolecular electronic energy transfer in coumarin bichromophoric molecules. An investigation by multifrequency phase modulation fluorometry", *Chem. Phys. Lett.*, 1985, 119: 217.

Mujurndar, et al., "Cyanine Dye Labeling Reagents: Sulfoindocyanine Succinimidyl Esters", *Bioconjugate Chemistry*, 1993, 4: 105-111.

Mujurndar, S.R., et al., "Cyanine-labeling reagents: Sulfobenzindocyanine Succinimidyl Esters", *Bioconjugate Chem.*, 1996, 7: 356-362.

Nakagaki, R., et al., "Photochemistry of bichromophoric chian molecules containing electron donor and acceptor moieties. Dependence of reaction pathways on the nitrophenoxy)alkyl)arulines", *Chem. Phys. Lett.*, 1985, 121: 262- 266.

Oliver, a.M., et al., "Strong Effects of the Bridge Configuration on Photoinduced Charge Separation in Rigidly Linked Donor-Acceptor Systems", *Chemical Physical Letters*, Sep. 1988, 150: 366-373.

Pispisa, B., et al., "Photophysical behavior or Poly(L-lysine) carrying Porphyrin and Naphthyl Chromophors", *Biopolymers*, 1994, 34: 435-442.

Prathapan, S., et al., "Building-block synthesis of porphyrin light0harvesting arrays", *J. Am. Chem. Soc.*, 1993, 115(16): 7519-7520.

Prober, J.M., et al., "A system for rapid DNA sequencing with fluorescent chain-terminating dideoxynucleotides", *Science*, 1987, 238: 238-341.

Rice, K.G., et al., "Interterminal Distance and Flexibility of a Triantennary Glycopeptide As Measured by Resonance Energy Transfer", *Biochemistry* 1991, 30: 6646-6655.

Sauer, M., et al., "Design of Multiplex Dyes", *Ber. Bun. Gesell. Phys. Chem.*, 1993, 97: 1734-1737.

Schaefer, F.P., *Chem. Phys. Lett.*, 1978, 56: 455.

Schaefer, F.P., et al., "Intermolecular TT-energy transfer in bifluorophoric laser dyes", *Appl. Phys. B.*, 1982, B28(1): 37-41 .

Scherer, T., et al., "Comparison of Flexibly and Rigidly Bridged Donor-Acceptor Systems; Solvent Induced Switching Between Folded and Extended Emissive Charge-Transfer States", *Recueil des Travaux Chimiques des Pays-Bas*, 1991, 110: 95-96.

Schnepp, O., et al., "Intramolecular energy transfer in a naphthalene-anthracene system", *J. Am. Chem. Soc.*, 1962, 84:172.

Scholes, G.D., et al., "Intramolecular Electronic Energy Transfer between Rigidly Linked Napthalene and Anthracene Chromophores", *Journal of Physical Chemistry*, 1993, 97: 11871-11876.

Selvin, P.R., "Fluorescence Resonance Energy Transfer", *Methods in Enzymology*, 1995, 246: 300-335.

Seth, J., et al., "Investigation of electronic communication in multi-porphyrin light-harvesting arrays", *J. Am. Chem. Soc.*, 1994, 116(23): 10578-10592.

Shipchandler, M.T., et al., "4'-[Aminomethyl]fluorescein and its N-alkyl derivatives: useful reagents in immunodiagnostic techniques", *Anal. Biochem.*, Apr. 1987, 162(1): 89-101.

Speiser, S., et al., "Intramolecular electronic energy transfer via exchange interaction in bichromophoric molecules", *Chem. Phys. Lett.*, 1983, 102, 88-94.

Stenzel, R., et al., "Cross-Reactivity of AntiODigoxin Antibodies with Digitoxin Depends on Tracer Structure", *Clin. Chem.*, 1992, 38(11): 2228-2232.

Stryer, L., et al., "Energy Transfer: A Spectroscopic Ruler", *Proc. Natl. Acad. Sci. USA*, 1967, 58: 719-726.

Tamaki, T., "Intramolecular interaction between the phenol and indole chromophore", *Bull. Soc. Chem.*, Japan, 1973, 46: 2527.

Tanke, H. "What's new from the field: Current developments in flow cytometry and fluorescent labels", ADVERTISEMENT, *Molecular Probes, Inc.*, 1989, pp. 63-65.

Thornton, N.B., et al., "Chromophore-quencher Probes for DNA", *New Journal of Chemistry*, 1996, 20: 791-800.

Tian, H., et al., "Bichromophoric Rhodamine Dyes and Their Fluorescence Properties", *Dyes Pigm.*, 1994, 26: 159-165.

Tyagi, S., et al., "Molecular Beacons: Probes that Fluorescence upon Hybridization", *Nature Biotechnology*, Mar. 1996, 14:303-368.

Valeur, B., et al., "Calculation of the Distribution of Donor-Acceptor Distances in Flexible Bichromophoric Molecules. Application to Intramolecular Transfer of Excitation Energy", *The Journal of Physical Chemistry*, Dec. 1989, 93:6073-6079.

Vamosi, G., et al., "Fluorescence characteristics of 5-carboxyetramethylrhodamine linked covalently to the 5' end of oligonucelotides: multiple conformers of single0stranded and double-stranded dye-DNA complexes", *Biophys. J.*, 1996, 71: 972-994.

Wagner, R. W., et al., "Synthesis of facially encumbered porphyrins. An approach to light harvesting antenna complexes", *Tetrahedron Letters*, 1991, 32(14): 1703-1706.

Wagner, R.W., et al., "A molecular photonic wire", *J. Am. Chem. Soc.*, 1994, 116(21): 9759-9760.

Wagner, R.W., et al., "Self-assembly of molecular devices containing a ferrocene, a porphyrin and a quinone in a triple macrocyclic architecture", *J. Chem. Soc. Chem. Commun.*, 1991, No. 20, pp. 1463-1466.

Wagner, R.W., et al., "Synthesis of porphyrins tailored with eight facially-encumbering groups. An approach to solid state light harvesting complexes", *Tetrahedron*, 1994, 50(38): 11097-11112.

Wang, Y., et al., "Photochemical Probes of Intramolecular Electron and Energy Transfer", *Chemical Physics*, Mar. 1993, 176: 305-319.

Wasielewski, M.R., et al., "Ultrafast carotenoid to pheophorbide energy transfer in a biomimetic model for antenna function in photosynthesis", *Nature*, 1986, 322: 570-572.

Weber, G., et al., "Fluorescence excitation spectrum of organic compounds in solution part I. Systems with Quantum yield independent of exciting wavelength", *Trans. Faraday Soc.*, 1958, 54: 640.

Weiss, S., et al., "Probing the interaction between single molecules: fluorescence resonance energy transfer between a single donor and a single acceptor", *Conference title: QELS '96. Summaries of papers presented at the quantum electronics and laser science Conference.* vol. 10, 1996 Technical Digest Series. Conference Edition (IEEE Cat. No. 96CH35902).

Wu, P., et al., "Resonance energy transfer: methods and applications", *Anal. Biochem.*, Apr. 1994, 218(1): 1-13.

Yang, J., et al., "Fluorescence energy transfer studies in a cross-linked polyurethane network", *Can. J. Chem.*, 1995, 73:1823-1830.

Yuan, P., "Photophysical behavior in bichromophores and energy transfer basic indicators", Ph.D. Dissertation, 1991, Tufts University.

Zheng, Z., et al., "Fluorescence energy-transfer cyanine heterodimers with High affinity for double-stranded DNA. Ii. Applications to multiplex restriction fragment sizing", *Anal. Biochem.*, 1995, 231: 256-260.

Zhu, Z., et al., "Directly labeled DNA probes using fluorescent nucleotides with different length linkers", *Nucleic Acids Research*, 1994, 22(16): 3418-3422.

Zlokarnik et al., "Quantitation of Transcription and Clonal Selection of Single Living Cells with β-Lactamase as Reporter," Jan. 2, 1998, Science 279:84-88.

* cited by examiner

FIGURE 2
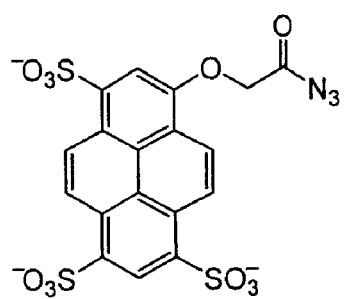
DYE110
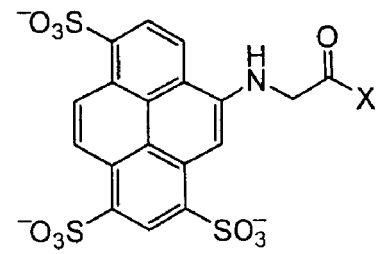
DYE122
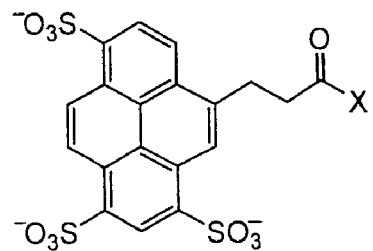
DYE124
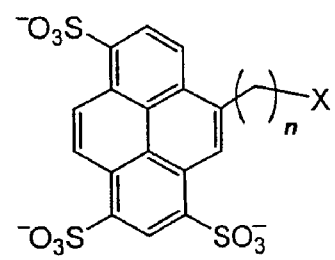
DYE126

FIGURE 3
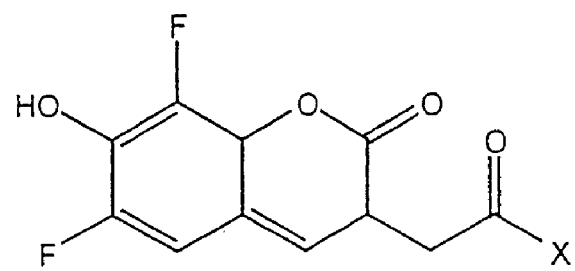
DYE112
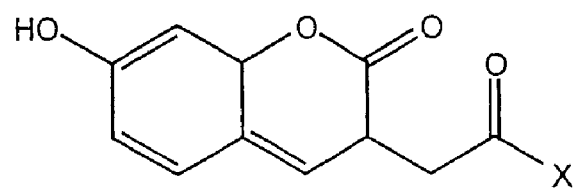
DYE114
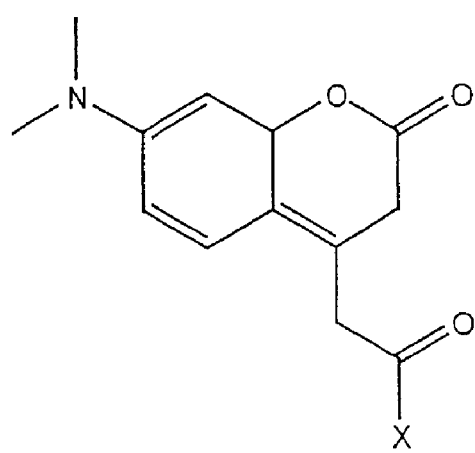
DYE116

DYE118

FIGURE 6
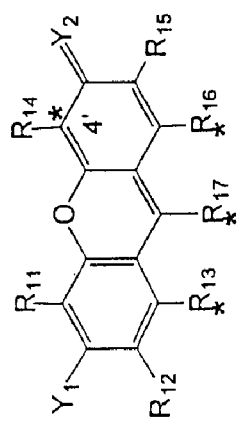
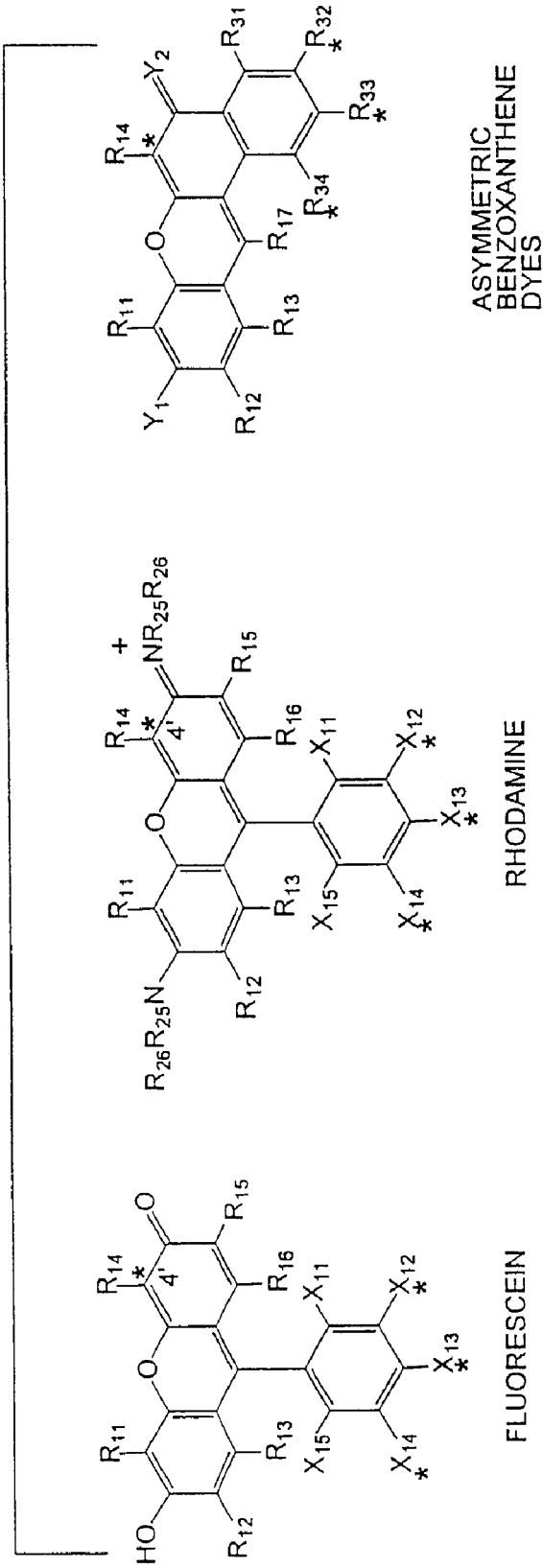

FIGURE 7A
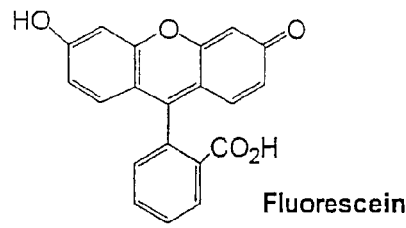
Fluorescein
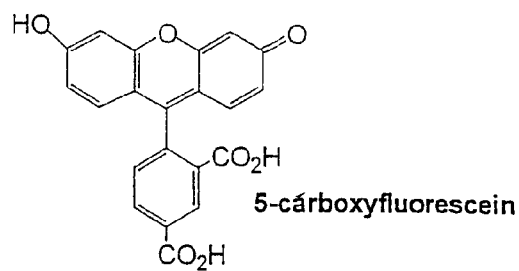
5-carboxyfluorescein
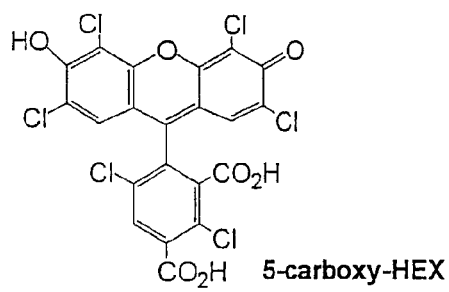
5-carboxy-HEX
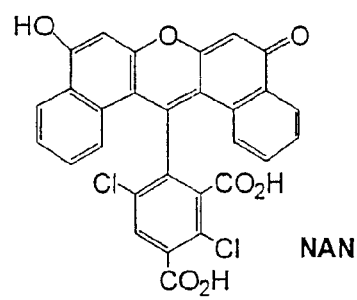
NAN
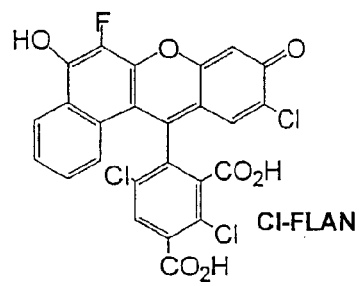
CI-FLAN
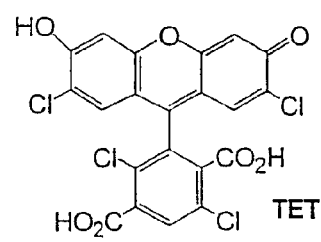
TET
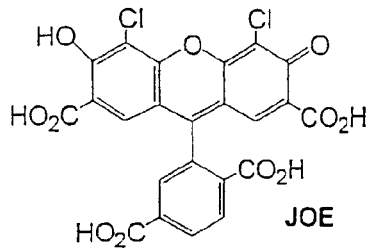
JOE
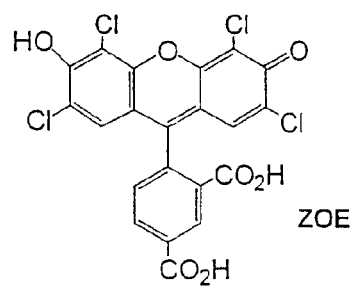
ZOE
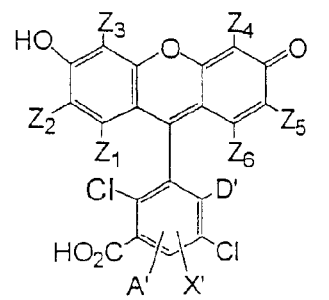
4,7-Dichlorofluorescein
(See Pat. No. 5,188,934)
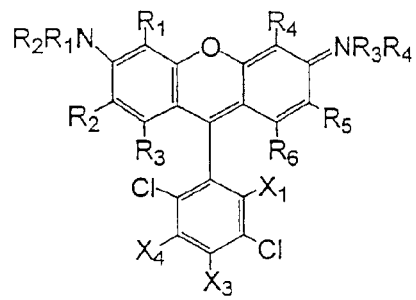
4,7-Dichlororhodamine FIGURE 7B
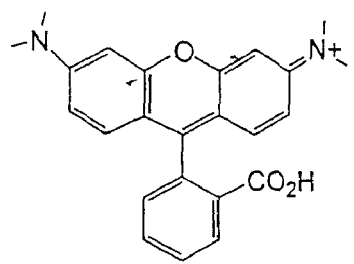
Rhodamine
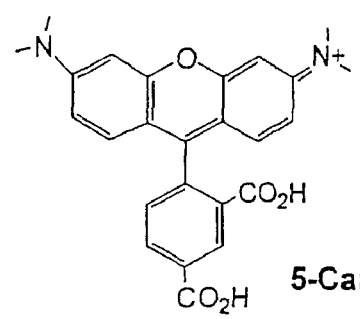
5-Carboxyrhodamine
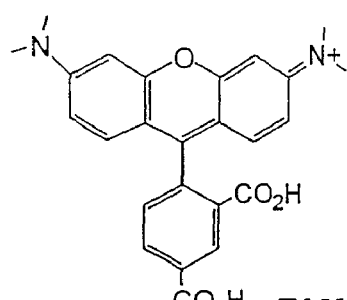
TAMRA
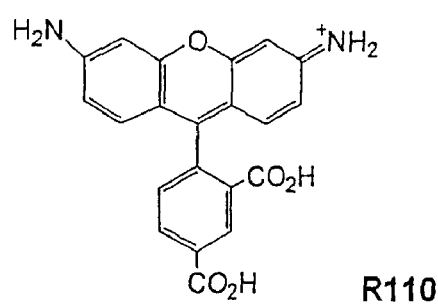
R110
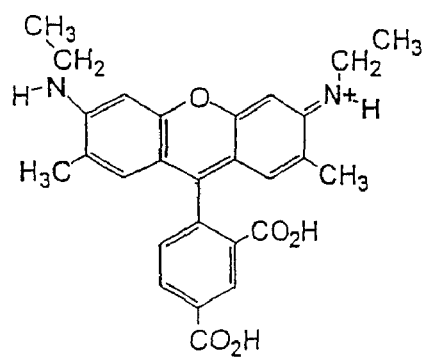
RG6
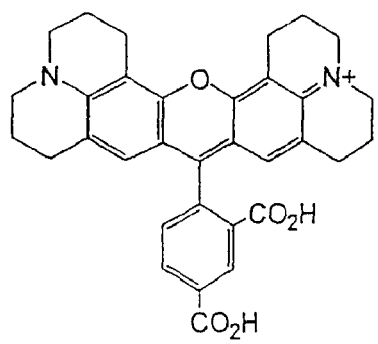
ROX

DYE104

DYE108

Excitation and Emission Spectra of pyrenetrisulfonate-d-Rox (DYE 120) in water

UV EXCITABLE FLUORESCENT ENERGY TRANSFER DYES

BACKGROUND OF THE INVENTION

1. Field of the Invention

The present invention relates to fluorescent dyes and, more specifically, energy transfer fluorescent dyes and their use.

2. Description of Related Art

A variety of fluorescent dyes have been developed, for labeling and detecting components in a sample. In general, fluorescent dyes preferably have a high quantum yield and a large extinction coefficient so that the dye may be used to detect small quantities of the component being detected. Fluorescent dyes also preferably have a large Stokes' shift (i.e., the difference between the wavelength at which the dye has maximum absorbance and the wavelength at which the dye has maximum emission) so that the fluorescent emission is readily distinguished from the light source used to excite the dye.

One class of fluorescent dyes which has been developed is energy transfer fluorescent dyes. In general, energy transfer fluorescent dyes include a donor fluorophore and an acceptor fluorophore. In these dyes, when the donor and acceptor fluorophores are positioned in proximity with each other and with the proper orientation relative to each other, the energy emission from the donor fluorophore is absorbed by the acceptor fluorophore and causes the acceptor fluorophore to fluoresce. It is therefore important that the excited donor fluorophore be able to efficiently absorb the excitation energy of the donor fluorophore and efficiently transfer the energy to the acceptor fluorophore.

A variety of energy transfer fluorescent dyes have been described in the literature. For example, U.S. Pat. No. 4,996,143 and WO 95/21266 describe energy transfer fluorescent dyes where the donor and acceptor fluorophores are linked by an oligonucleotide chain. Lee, et al., *Nucleic Acids Research* 20:10 2471-2483 (1992) describes an energy transfer fluorescent dye which includes 5-carboxy rhodamine linked to 4'-aminomethyl-5-carboxy fluorescein by the 4'-aminomethyl substituent on fluorescein. U.S. Pat. No. 5,847,162 describes additional classes of energy transfer dyes.

Several diagnostic and analytical assays have been developed which involve the detection of multiple components in a sample using fluorescent dyes, e.g. flow cytometry (Lanier, et al., *J. Immunol.* 132 151-156 (1984)); chromosome analysis (Gray, et al., *Chromosoma* 73 9-27 (1979)); and DNA sequencing. For these assays, it is desirable to simultaneously employ a set of two or more spectrally resolvable fluorescent dyes so that more than one target substance can be detected in the sample at the same time. Simultaneous detection of multiple components in a sample using multiple dyes reduces the time required to serially detect individual components in a sample. In the case of multi-loci DNA probe assays, the use of multiple spectrally resolvable fluorescent dyes reduces the number of reaction tubes that are needed, thereby simplifying the experimental protocols and facilitating the manufacturing of application-specific kits. In the case of automated DNA sequencing, the use of multiple spectrally resolvable fluorescent dyes allows for the analysis of all four bases in a single lane thereby increasing throughput over single-color methods and eliminating uncertainties associated with inter-lane electrophoretic mobility variations. Connell, et al., *Biotechniques* 5 342-348 (1987); Prober, et al., *Science* 238 336-341 (1987), Smith, et al., *Nature* 321 674-679 (1986); and Ansorge, et al., *Nucleic Acids Research* 15 4593-4602 (1989).

There are several difficulties associated with obtaining a set of fluorescent dyes for simultaneously detecting multiple target substances in a sample, particularly for analyses requiring an electrophoretic separation and treatment with enzymes, e.g., DNA sequencing. For example, each dye in the set must be spectrally resolvable from the other dyes. It is difficult to find a collection of dyes whose emission spectra are spectrally resolved, since the typical emission band halfwidth for organic fluorescent dyes is about 40-80 nanometers (nm) and the width of the available spectrum is limited by the excitation light source. As used herein the term "spectral resolution" in reference to a set of dyes means that the fluorescent emission bands of the dyes are sufficiently distinct, i.e., sufficiently non-overlapping, that reagents to which the respective dyes are attached, e.g. polynucleotides, can be distinguished on the basis of the fluorescent signal generated by the respective dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811,218, or in Wheeless et al, pgs. 21-76, in *Flow Cytometry: Instrumentation and Data Analysis* (Academic Press, New York, 1985).

The fluorescent signal of each of the dyes must also be sufficiently strong so that each component can be detected with sufficient sensitivity. For example, in the case of DNA sequencing, increased sample loading can not compensate for low fluorescence efficiencies, Pringle et al., *DNA Core Facilities Newsletter*, 1 15-21 (1988). The fluorescent signal generated by a dye is generally greatest when the dye is excited at its absorbance maximum. It is therefore preferred that each dye be excited at about its absorbance maximum.

A further difficulty associated with the use of a set of dyes is that the dyes generally do not have the same absorbance maximum. When a set of dyes are used which do not have the same absorbance maximum, a trade off is created between the higher cost associated with providing multiple light sources to excite each dye at its absorbance maximum, and the lower sensitivity arising from each dye not being excited at its absorbance maximum.

In addition to the above difficulties, the charge, molecular size, and conformation of the dyes must not adversely affect the electrophoretic mobilities of the fragments. The fluorescent dyes must also be compatible with the chemistry used to create or manipulate the fragments, e.g., DNA synthesis solvents and reagents, buffers, polymerase enzymes, ligase enzymes, and the like.

Because of the multiple constraints on developing a set of dyes for multicolor applications, particularly in the area of four color DNA sequencing, only a few sets of fluorescent dyes have been developed. Connell, et al., *Biotechniques* 5 342-348 (1987); Prober, et al., *Science* 238 336-341 (1987); and Smith, et al., *Nature* 321 674-679 (1986); and U.S. Pat. No. 5,847,162.

Energy transfer fluorescent dyes possess several features which make them attractive for use in the simultaneous detection of multiple target substances in a sample, such as in DNA sequencing. For example, a single donor fluorophore can be used in a set of energy transfer fluorescent dyes so that each dye has strong absorption at a common wavelength. Then, by varying the acceptor fluorophore in the energy transfer dye, a series of energy transfer dyes having spectrally resolvable fluorescence emissions can be generated.

Energy transfer fluorescent dyes also provide a larger effective Stokes' shift than non-energy transfer fluorescent dyes. This is because the Stokes' shift for an energy transfer fluorescent dye is based on the difference between the wavelength at which the donor fluorophore maximally absorbs light and the wavelength at which the acceptor fluorophore maximally emits light. In general, a need exists for fluorescent dyes having larger Stokes' shifts.

The sensitivity of any assay using a fluorescent dye is dependent on the strength of the fluorescent signal generated by the fluorescent dye. A need therefore exists for fluorescent dyes which have a strong fluorescence signal. With regard to energy transfer fluorescent dyes, the fluorescence signal strength of these dyes is dependent on how efficiently the acceptor fluorophore absorbs the energy emission of the donor fluorophore.

SUMMARY OF THE INVENTION

The present invention relates to energy transfer dyes which can be used with shorter wavelength light sources. The present invention also relates to reagents which include the energy transfer dyes of the present invention. The present invention also relates to methods which use dyes and reagents adapted to shorter wavelength light sources. Kits are also provided which include the dyes and reagents.

Energy transfer dyes are provided which include a donor dye with an absorption maxima at a wavelength between about 250 to 450 nm and an acceptor dye which is capable of absorbing energy from the donor dye.

It is noted that energy transfer may occur by a variety of mechanisms. For example, the emission of the donor dye does not need to overlap with the absorbance of the acceptor dye for many of the dyes of the present invention.

In one variation, the donor dye has an absorption maxima between about 300 and 450 nm, more preferably between about 350 and 400 nm.

The acceptor dye preferably has an emission maxima greater than about 500 nm. In one variation, the acceptor dye has an emission maxima at a wavelength greater than about 550 nm. The acceptor dye may also have an emission maxima at a wavelength between about 500 and 700 nm. The acceptor dye may also be selected relative to the donor dye such that the acceptor dye has an emission maxima at a wavelength at least about 150 nm greater than the absorption maxima of the donor dye.

In another embodiment of the present invention, the energy transfer dye has a donor dye which is a member of a class of dyes having a coumarin or pyrene ring structure and an acceptor dye which is capable of absorbing energy from the donor dye.

In one variation of this embodiment, the donor dye has an absorption maxima between about 250 and 450 nm, preferably between about 300 and 450 nm, and more preferably between about 350 and 400 nm.

In another variation of this embodiment, the acceptor dye has an emission maxima at a wavelength greater than about 500 nm, and optionally more than 550 nm. The acceptor dye may also have an emission maxima at a wavelength between about 500 and 700 nm. The acceptor dye may also be selected relative to the donor dye such that the acceptor dye has an emission maxima at a wavelength at least about 150 nm greater than the absorption maxima of the donor dye.

An energy transfer dye according to the present invention may also have the structure of "antennae" dyes or dendrimers in which large numbers of donor dyes are coupled to one acceptor dye where the donor dye either has an absorption maxima between 250 and 450 nm or has a coumarin or pyrene ring structure.

The present invention also relates to fluorescent reagents containing any of the energy transfer dyes of the present invention. In general, these reagents include any molecule or material to which the energy transfer dyes of the invention can be attached. The presence of the reagent is detected by the fluorescence of the energy transfer dye. One use of the reagents of the present invention is in nucleic acid sequencing.

Examples of classes of the fluorescent reagents include deoxynucleosides and mono-, di- or triphosphates of a deoxynucleoside labeled with an energy transfer dye. Examples of deoxynucleotides include deoxycytosine, deoxyadenosine, deoxyguanosine or deoxythymidine, and analogs and derivatives thereof.

Other classes of the reagents include analogs and derivatives of deoxynucleotides which are not extended at the 3' position by a polymerase. A variety of analogs and derivatives have been developed which include a moiety at the 3' position to prevent extension including halides, acetyl, benzyl and azide groups. Dideoxynucleosides and dideoxynucleoside mono-, di- or triphosphates which cannot be extended have also been developed. Examples of dideoxynucleotides include dideoxycytosine, dideoxyadenosine, dideoxyguanosine or dideoxythymidine, and analogs and derivatives thereof.

The fluorescently labeled reagent may also be an oligonucleotide. The oligonucleotide may have a 3' end which is extendable by using a nucleotide polymerase. Such a labeled oligonucleotide may be used, for example, as a dye-labeled primer in nucleic acid sequencing.

The present invention also relates to methods which use the energy transfer dyes and reagents of the present invention. In one embodiment, the method includes forming a series of different sized oligonucleotides labeled with an energy transfer dye of the present invention, separating the series of labeled oligonucleotides based on size and detecting the separated labeled oligonucleotides based on the fluorescence of the energy transfer dye.

In another embodiment, the method includes forming a mixture of extended labeled primers by hybridizing a nucleic acid with an oligonucleotide primer in the presence of deoxynucleoside triphosphates, at least one dideoxynucleoside triphosphate and a DNA polymerase, the DNA polymerase extending the primer with the deoxynucleoside triphosphates until a dideoxynucleoside triphosphate is incorporated which terminates extension of the primer. Once terminated, the mixture of extended primers are separated and the separated extended primers detected by detecting an energy transfer dye of the present invention that was incorporated onto either the oligonucleotide primer, a deoxynucleotide triphosphate, or a dideoxynuceotide triphosphate.

The present invention also relates to methods for sequencing a nucleic acid using the energy transfer dyes of the present invention. In one embodiment, the method includes forming a mixture of extended labeled primers by hybridizing a nucleic acid sequence with an oligonucleotide primer in the presence of deoxynucleoside triphosphates, at least one dideoxynucleoside triphosphate and a DNA polymerase. The oligonucleotide primer and/or the dideoxynucleotide is labeled with an energy transfer dye of the present invention. The DNA polymerase is used to extend the primer with the deoxynucleoside triphosphates until a dideoxynucleoside triphosphate is incorporated which terminates extension of the primer. The mixture of extended primers are then separated and the sequence of the nucleic acid determined by detecting the energy transfer dye on the extended primer.

The present invention also relates to methods for detecting oligonucleotides and reagents labeled with energy transfer dyes using shorter wavelength light sources. The light sources used in these methods preferably provide energy at a wavelength less than 450 nm. In one variation, the light source provides energy at a wavelength between about 250 and 450 nm, preferably between about 300 and 450 nm, and most preferably between about 350 and 450 nm. In one particular embodiment, the light source used provides energy at about 400 nm.

In one embodiment, the method includes forming a series of different sized oligonucleotides labeled with an energy transfer dye, separating the series of labeled oligonucleotides based on size and detecting the separated labeled oligonucleotides based on the fluorescence of the energy transfer dye upon exposure to a shorter wavelength light source.

In another embodiment, the method includes forming a mixture of extended labeled primers by hybridizing a nucleic acid with an oligonucleotide primer in the presence of deoxynucleoside triphosphates, at least one dideoxynucleoside triphosphate and a DNA polymerase, the DNA polymerase extending the primer with the deoxynucleoside triphosphates until a dideoxynucleoside triphosphate is incorporated which terminates extension of the primer. Once terminated, the mixture of extended primers are separated. The separated extended primers are detected by exposing the extended primer to light having a wavelength between about 250 and 450 nm and measuring light emitted by an energy transfer dye at a wavelength greater than about 500 nm. The energy transfer dye is incorporated onto either the oligonucleotide primer, a deoxynucleotide triphosphate, or a dideoxynuceotide triphosphate.

The present invention also relates to methods for sequencing a nucleic acid using a shorter wavelength light source. In one embodiment, the method includes forming a mixture of extended labeled primers by hybridizing a nucleic acid sequence with an oligonucleotide primer in the presence of deoxynucleoside triphosphates, at least one dideoxynucleoside triphosphate and a DNA polymerase. The oligonucleotide primer and/or the dideoxynucleotide is labeled with an energy transfer dye adapted for use with a shorter wavelength light source. The DNA polymerase is used to extend the primer with the deoxynucleoside triphosphates until a dideoxynucleoside triphosphate is incorporated which terminates extension of the primer. The mixture of extended primers are then separated and the sequence of the nucleic acid determined by exposing the extended primer to light having a wavelength between about 250 and 450 nm and measuring light emitted by the energy transfer dye at a wavelength greater than about 500 nm.

In a preferred variation of the embodiment, the extended primer is exposed to light having a wavelength between about 300 and 450 nm. The extended primer may also be exposed to light having a wavelength between about 350 and 400 nm. In another preferred variation of the embodiment, the light emitted by the energy transfer dye has a wavelength greater than about 550 nm. The light emitted by the energy transfer dye may also have a wavelength between about 500 and 700 nm. In another embodiment, the light emitted by the energy transfer dye has a wavelength at least about 150 nm greater than the wavelength of the light to which the extended primer is exposed.

The present invention also relates to kits containing the dyes and reagents for performing DNA sequencing using the dyes and reagents of the present invention. A kit may include a set of 2, 3, 4 or more energy transfer dyes or reagents of the present invention. Optionally the kits may further include a nucleotide polymerase, additional nucleotides and/or reagents useful for performing nucleic acid sequencing.

BRIEF DESCRIPTION OF THE FIGURES

FIG. 2 illustrates examples of donor dyes which include a pyrene ring structure.

FIG. 3 illustrates examples of donor dyes which include a coumarin ring structure.

FIG. 6 illustrates the general structure of xanthene dyes and classes of xanthene dyes like fluorescein, rhodamine and asymmetric benzoxanthene.

FIG. 7 illustrates structures of acceptor dyes which may be used in the dyes of the present invention.

DETAILED DESCRIPTION

The present invention relates to energy transfer dyes which may be used with shorter wavelength light sources. For example, the energy transfer dyes are preferably adapted to be excited at wavelengths between about 250 and 450 nm. The present invention also relates to reagents which include the energy transfer dyes of the present invention. The present invention further relates to methods which use the dyes and reagents. Kits are also provided which include the dyes and reagents.

I. Energy Transfer Dyes

The energy transfer dyes of the present invention include a donor dye and an acceptor dye which is capable of emitting energy in response to absorbing energy from the donor dye.

In one embodiment, the energy transfer dyes may be excited at wavelengths between about 250 and 450 nm. According to this embodiment, the donor dye preferably has an absorption maxima at a wavelength between about 250 to 450 nm, more preferably between about 300 and 450 nm, and most preferably between about 350 and 450 nm.

In another embodiment, the energy transfer dyes include an donor dye having a coumarin or pyrene ring structure.

The acceptor dye may be any dye which is capable of absorbing energy from the donor dye. In one embodiment, the acceptor dye has an emission maxima greater than about 500 nm, more preferably greater than 550 nm. In another embodiment, the acceptor dye has an emission maxima between about 500 and 700 nm. In another embodiment, the acceptor dye is selected such that it has an emission maxima at a wavelength at least about 150 nm greater than the absorption maxima of the donor dye.

The energy transfer dyes may also include a linker which couples the donor dye to the acceptor dye. The linker preferably couples the donor dye to the acceptor dye such that the acceptor dye is able to absorb substantially all of the energy by the donor dye.

Figure 1:
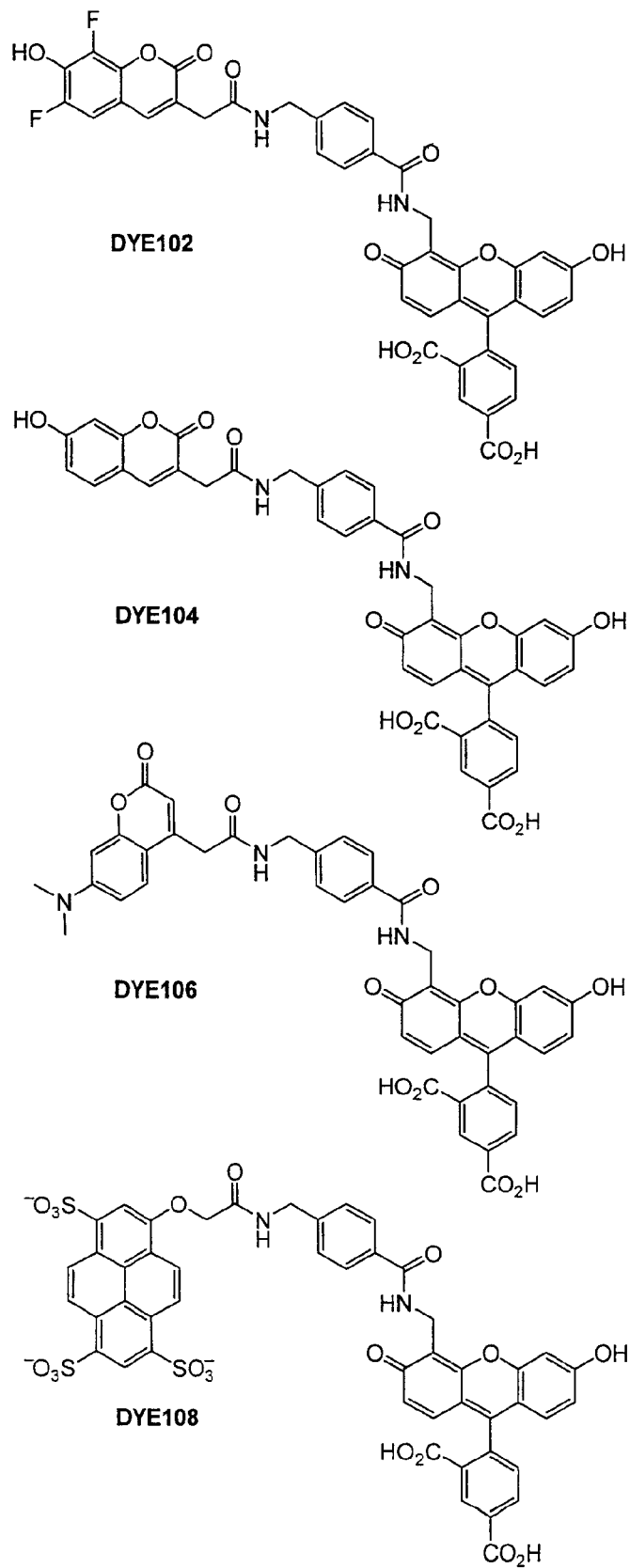
FIG. 1 illustrates examples of energy transfer dyes according to the present invention.

Particular examples of energy transfer dyes of the present invention are illustrated in FIG. 1. In these examples 5-carboxyfluorescein, which has an emission maxima of 523 nm, is used as the acceptor dye. Coumarin-based donor dyes DYE116, which has an absorption maxima at 376 nm, DYE114 (absorption maximum=328 nm), and DYE112 (absorption maximum=362 nm) or pyrene-based donor dye DYE110 (absorption maximum=396 nm) are conjugated to a 5-carboxyfluorescein acceptor derivatized with a 4-aminomethylbenzoic linker (5CF-B). The structures of the 5CF-B conjugates, DYE102, DYE104, DYE106, and DYE108, are shown in FIG. 1.

A. Donor Dye

In one embodiment, the donor dye has an absorption maxima at a wavelength between about 250 to 450 nm, more preferably between about 300 and 450 nm, most preferably between about 350 and 400 nm.

In another embodiment, the donor dye has a pyrene ring structure. As used herein, pyrene dyes include all molecules including the general structure

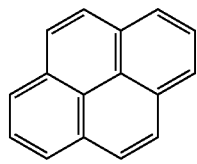

The present invention is intended to encompass all pyrene dyes since all may be used in the present invention. Particular examples of pyrene dyes, DYE110, DYE122, DYE124 and DYE126, are illustrated in FIG. 2. In the figure, X is a functional group which may be used to attach substituents, such as the acceptor dye, to the donor dye.

In another embodiment, the donor dye has a coumarin ring structure. As used herein, coumarin dyes include all molecules including the general structure.

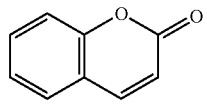

The present invention is intended to encompass all coumarin dyes since all may be used in the present invention. Particular examples of coumarin dyes are illustrated in FIG. 3. In the figure, X is a functional group which may be used to attach substituents, such as the acceptor dye, to the donor dye.

Figure 4:
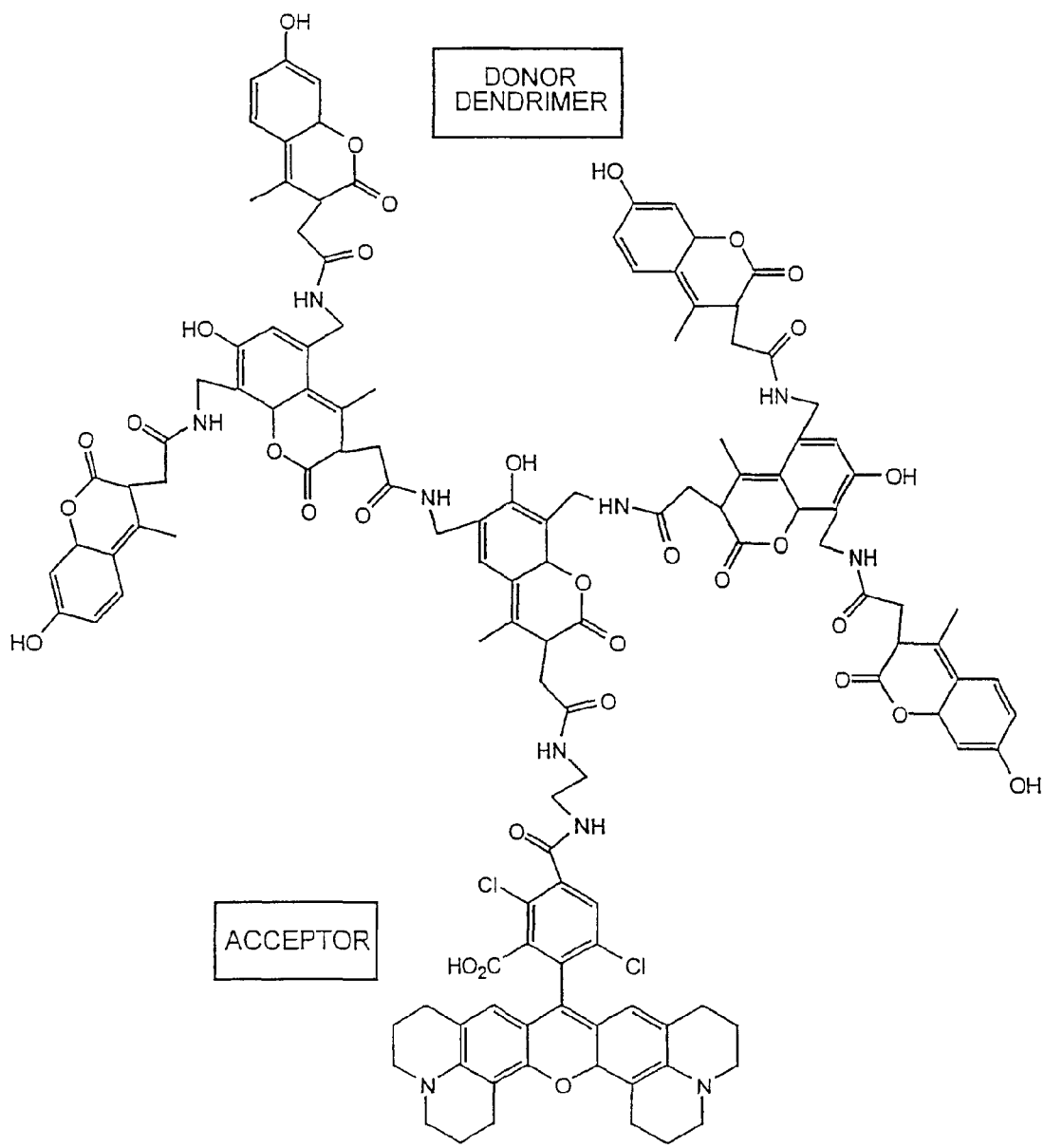
FIG. 4 illustrates the structure of a dendrimer energy-transfer dye.

The present invention also relates to energy transfer dyes where multiple donor dyes are coupled to an acceptor dye. Coumarin dyes are water-soluble and coumarin conjugates show much better quantum yields than larger dyes, for which the quantum yields in water are about ⅓ that of free acceptor dyes. The present invention utilizes the small size and solubility of the coumarins to synthesize "antennae" dyes or dendrimers in which large numbers of donor dyes are coupled to one acceptor dye. An example of a dendrimer energy transfer dye (DYE118) is shown in FIG. 4.

B. Acceptor Dye

The acceptor dye may be any dye which is capable of absorbing energy from the donor dye. In one embodiment, the acceptor dye has an emission maxima greater than about 500 nm, more preferably greater than 550 nm. In another embodiment, the acceptor dye has an emission maxima between about 500 and 700 nm. In another embodiment, the acceptor dye is selected such that it has an emission maxima at a wavelength at least about 150 nm greater than the absorption maxima of the donor dye.

Figure 5:
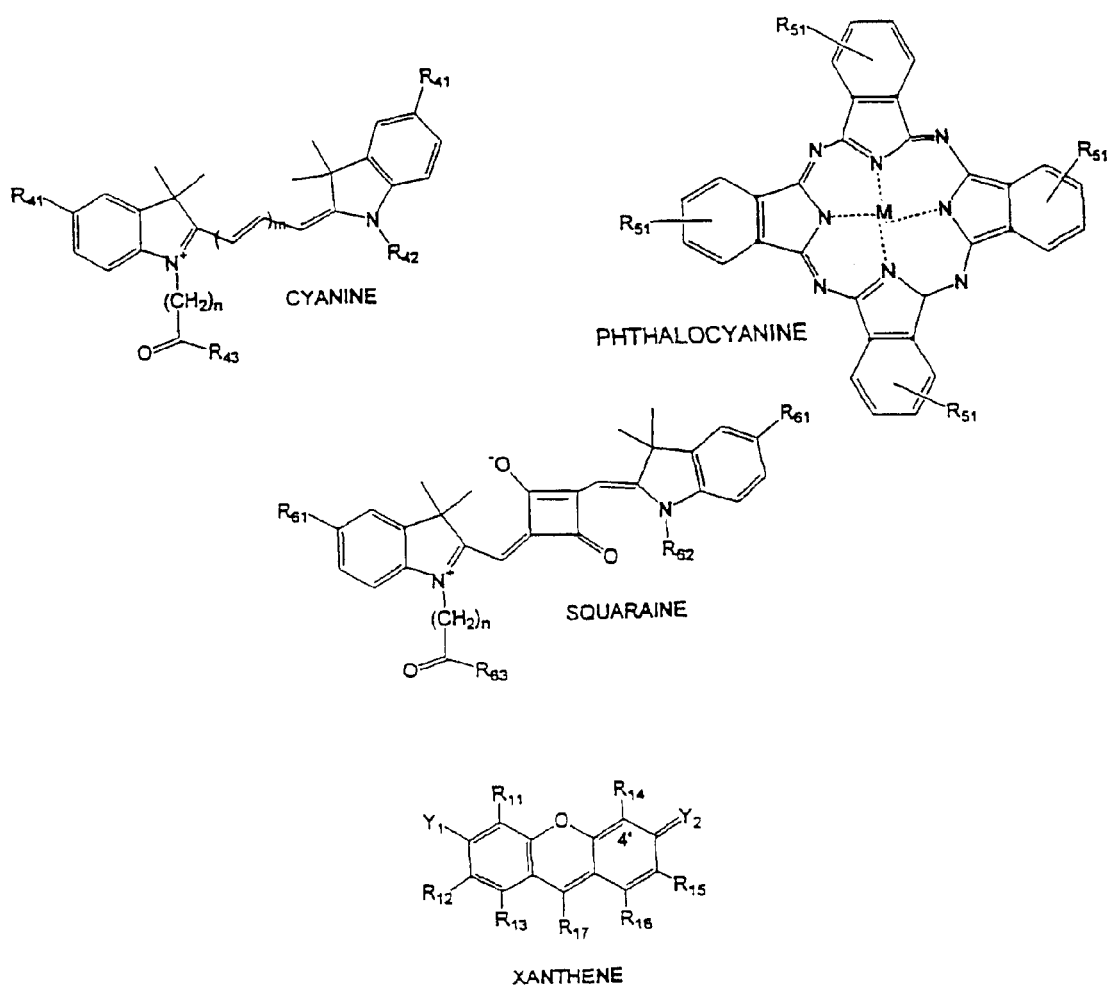
FIG. 5 illustrates classes of acceptor dyes including xanthene dyes, cyanine dyes, phthalocyanine dyes and squaraine dyes.

Examples of classes of acceptor dyes which may be used in the energy transfer fluorescent dye of this embodiment include, but are not limited to, xanthene dyes, cyanine dyes, phthalocyanine dyes and squaraine dyes. The general structures of these dyes are illustrated in FIG. 5. The substituents illustrated on these dyes may be selected from the wide variety of substituents which may be incorporated onto these different classes of dyes since all dyes having the general xanthene, fluorescein, rhodamine, asymmetric benzoxanthene, cyanine, phthalocyanine and squaraine ring structures are intended to fall within the scope of this invention.

One particular class of acceptor dyes which may be used in the energy transfer dyes of the present invention are xanthene dyes. As used herein, xanthene dyes include all molecules having the general structure illustrated in FIG. 6 where $Y_1$ and $Y_2$ taken separately are either hydroxyl, oxygen, iminium or amine, the iminium and amine preferably being a tertiary iminium or amine. Examples of classes of xanthene dyes are fluorescein, rhodamine and asymmetric benzoxanthene classes of dyes which are also illustrated in FIG. 6. The substituents illustrated on these dyes may be selected from the wide variety of substituents which may be incorporated onto these different classes of dyes since all dyes having the general xanthene, fluorescein, rhodamine, and asymmetric benzoxanthene ring structures are intended to fall within the scope of this invention. Fluorescein and rhodamine dyes may be linked to a substituent, such as an acceptor dye, a nucleoside, or an oligonucleotide, in a variety of locations. Illustrated with an asterik "*" in FIG. 6 are preferred locations for substitutions.

Fluorescein and rhodamine classes of dyes are members of a particular subclass of xanthene dyes where $R_{17}$ is a phenyl or substituted phenyl having the general formula

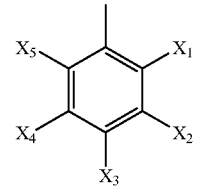

Substituents $X_1$-$X_5$ on the phenyl ring can include hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof. As illustrated in FIG. 5, dyes where $Y_1$ is hydroxyl and $Y_2$ is carboxyl are fluorescein dyes and where $Y_1$ is amine and $Y_2$ is iminium are rhodamine dyes.

$R_{11}$-$R_{17}$ may be any substituent which is compatible with the energy transfer dyes of the present invention, it being noted that the $R_{11}$-$R_{17}$ may be widely varied in order to alter the spectral and mobility properties of the dyes. Examples of $R_{11}$-$R_{17}$ substituents include, but not limited to hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof.

In one embodiment, $R_{15}$ and $R_{16}$ are taken together to form a substituted or unsubstituted benzene ring. This class of xanthene dyes are referred to herein as asymmetric benzoxanthene dyes and are described in U.S. Pat. No. 5,840,999, entitled Asymmetric Benzoxanthene Dyes, by Scott C. Benson, et al. which is incorporated herein by reference.

In one particular embodiment, the acceptor dye is a member of the class of dyes where $Y_1$ is amine, $Y_2$ is iminium, and $X_2$ and $X_5$ are chlorine, referred to herein as 4,7-dichlororhodamine dyes. Dyes falling within the 4,7-dichlororhodamine class of dyes and their synthesis are described in U.S. Pat. No. 5,847,162, entitled: "4,7-Dichlororhodamine Dyes" which is incorporated herein by reference.

$R_{11}$-$R_{17}$ and $X_1$-$X_5$ may also each independently be a linking moiety which may be used to attach the energy transfer dye to a reagent, such as a nucleotide, nucleoside or oligonucleotide. Examples of linking moieties include isothiocyanate, sulfonyl chloride, 4,6-dichlorotriazinylamine, succinimidyl ester, or other active carboxylate whenever the complementary functionality is amine. Preferably the linking group is maleimide, halo acetyl, or iodoacetamide whenever the complementary functionality is sulfhydryl. See R. Haugland, *Molecular Probes Handbook of Fluorescent Probes and Research Chemicals*, Molecular probes, Inc. (1992). In a particularly preferred embodiment, the linking group is an activated NHS ester formed from a carboxyl group on either the donor or acceptor dye which can be reacted with an aminohexyl-oligomer to form a dye labeled oligonucleotide primer.

As used here, alkyl denotes straight-chain and branched hydrocarbon moieties, i.e., methyl, ethyl, propyl, isopropyl, tert-butyl, isobutyl, sec-butyl, neopentyl, tert-pentyl, and the like. Substituted alkyl denotes an alkyl moiety substituted with any one of a variety of substituents, including, but not limited to hydroxy, amino, thio, cyano, nitro, sulfo, and the like. Haloalkyl denotes a substituted alkyl with one or more halogen atom substituents, usually fluoro, chloro, bromo, or iodo. Alkene denotes a hydocarbon wherein one or more of the carbon-carbon bonds are double bonds, and the non-double bonded carbons are alkyl or substituted alkyl. Alkyne denotes a hydocarbon where one or more of the carbons are bonded with a triple bond and where the non-triple bonded carbons are alkyl or substituted alkyl moieties. Sulfonate refers to moieties including a sulfur atom bonded to 3 oxygen atoms, including mono- and di-salts thereof, e.g., sodium sulfonate, potassium sulfonate, disodium sulfonate, and the like. Amino refers to moieties including a nitrogen atom bonded to 2 hydrogen atoms, alkyl moieties, or any combination thereof. Amido refers to moieties including a carbon atom double bonded to an oxygen atom and single bonded to an amino moiety. Nitrile refers to moieties including a carbon atom triple bonded to a nitrogen atom. Alkoxy refers to a moiety including an alkyl moiety single bonded to an oxygen atom. Aryl refers to single or multiple phenyl or substituted phenyl, e.g., benzene, naphthalene, anthracene, biphenyl, and the like.

In another embodiment, the acceptor dye is selected such that the acceptor dye has an emission maximum that is greater than about 500 nm and an emission maximum that is at least about 150 nm greater than the absorption maxima of the donor dye. This class of dyes of the present invention exhibit unusually large Stokes' shifts, as measured by the difference between the absorbance of the donor and the emission of the acceptor. In addition, these dyes exhibit efficient energy transfer in that minimal donor fluorescence is observed. Interestingly, energy is transferred from the donor to the acceptor in some of the dyes belonging to this class even though the absorbance spectrum of the acceptor dye does not overlap with the emission spectrum of the donor dye.

Particular examples of acceptor dyes which may be used in the dyes of the present invention include, but are not limited to isomers of carboxyfluorescein (e.g., 5 and 6 carboxy), 4,7-dichlorofluoresceins, 4,7-dichlororhodamines, fluoresceins, asymmetric benzoxanthene dyes, isomers of carboxy-HEX (e.g., 5 and 6 carboxy), NAN, CL-FLAN, TET, JOE, ZOE, rhodamine, isomers of carboxyrhodamine (e.g., 5 and 6 carboxy), isomers of carboxy R110 (e.g., 5 and 6 carboxy), isomers of carboxy R6G (e.g., 5 and 6 carboxy), 4,7-dichlorofluoresceins (See U.S. Pat. No. 5,188,934), 4,7-dichlororhodamines (See U.S. Pat. No. 5,847,162), asymmetric benzoxanthene dyes (See U.S. Pat. No. 5,840,999), isomers of N,N,N',N'-tetramethyl carboxyrhodamine (TAMRA) (e.g., 5 and 6 carboxy), isomers of carboxy-X-rhodamine (ROX) (e.g., 5 and 6 carboxy) and Cy5. Illustrated in FIG. 7 are the structures of these dyes.

C. Linkers

The donor dye may be joined with the acceptor dye using a wide variety of linkers which have been developed, all of which are intended to fall within the scope of the present invention. The energy transfer dyes which include a linker may generally be illustrated as

DONOR---LINKER---ACCEPTOR

In a preferred embodiment, the linker joins the donor dye to the acceptor dye such that the acceptor dye absorbs substantially all of the energy by the donor dye. While not being bound by theory, it is believed that the efficiency of energy transmission from the donor dye to the acceptor dye is dependent upon the separation between the dyes and relative orientation of the dyes. Described in U.S. Pat. No. 5,800,996 are linkers which have been found to be effective for providing a very high level of energy transfer between the donor and acceptor dye. U.S. Pat. No. 5,800,996 also describes methods for synthesizing dyes incorporating these linkers. U.S. Pat. No. 5,800,996 is incorporated herein by reference in its entirety.

In one particular embodiment, the linker used in the energy transfer dyes of the present invention is such that the acceptor dye absorbs substantially all of the excitation energy by the donor dye. Such linkers may include a functional group which provides structural rigidity to the linker. Examples of such functional groups include an alkene, diene, alkyne, a five and six membered ring having at least one unsaturated bond and/or having a fused ring structure.

Examples of functional groups with a five or six membered ring with at least one unsaturated bond and/or a fused ring structure include cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene.

Figure 8:
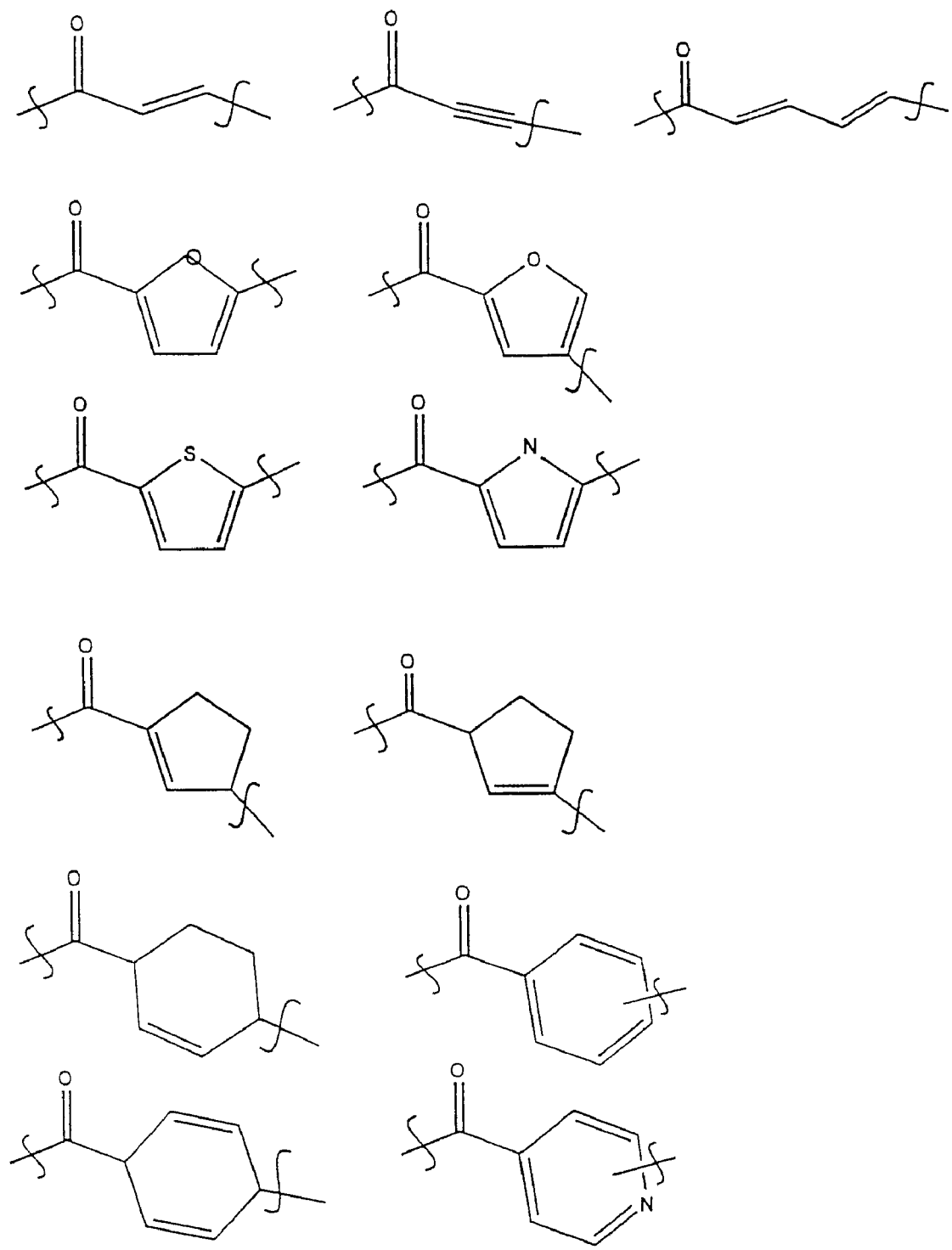
FIG. 8 illustrates examples of —C(O)$R_{22}$— subunits of linkers which may be used in the present invention.

One linker according to the present invention for linking a donor dye to an acceptor dye in an energy transfer dye includes the subunit structure —C(O)$R_{22}$—, where $R_{22}$ includes a functional group such as the ones described above which provides structural rigidity. FIG. 8 illustrates examples of —C(O)$R_{22}$— subunits of linkers which may be used in the linkers of the present invention.

One embodiment of this linker has the general structure —$R_{21}Z_1C(O)R_{22}R_{28}$—, where $R_{21}$ is a $C_{1-5}$ alkyl attached to the donor dye, C(O) is a carbonyl group $Z_1$ is either NH, sulfur or oxygen, $R_{22}$ is a substituent which includes an alkene, diene, alkyne, a five and six membered ring having at least one unsaturated bond or a fused ring structure which is attached to the carbonyl carbon, and $R_{28}$ includes a functional group which attaches the linker to the acceptor dye.

In one embodiment of this linker, the linker has the general structure —$R_{21}Z_1C(O)R_{22}R_{29}Z_2C(O)$— where $R_{21}$ and $R_{22}$ are as detailed above, $Z_1$ and $Z_2$ are each independently either NH, sulfur or oxygen, $R_{29}$ is a $C_{1-5}$ alkyl, and the terminal carbonyl group is attached to the ring structure of the acceptor dye. In the variation where $Z_2$ is nitrogen, the —C(O) $R_{22}R_{29}Z_2$— subunit forms an amino acid subunit.

A preferred embodiment of this linker is where $R_{21}$ and $R_{29}$ are methylene, $Z_1$ and $Z_2$ are NH, and $R_{22}$ is benzene.

In yet another variation, the linker has the general formula $R_{25}Z_3C(O)$ or $R_{25}Z_3C(O)R_{26}Z_4C(O)$ where $R_{25}$ is attached to the donor dye, C(O) is a carbonyl group and the terminal carbonyl group is attached to the acceptor dye, $R_{25}$ and $R_{26}$ are each selected from the group of $C_{1-4}$ alkyl, and $Z_3$ and $Z_4$ are each independently either NH, O or S.

In another variation of this embodiment, the linker includes a $R_{27}Z_5C(O)$ group where $R_{27}$ is a $C_{1-5}$ alkyl attached to the donor dye, $Z_5$ is either NH, sulfur or oxygen, and C(O) is a carbonyl group attached to the acceptor dye.

II. Reagents Including Energy Transfer Dyes Of The Present Invention

The present invention also relates to reagents which incorporate an energy transfer dye according to the present invention. As described in greater detail in Section III, these reagents may be used in a wide variety of methods for detecting the presence of a component in a sample.

The reagents of the present invention include any molecule or material to which the energy transfer dyes of the invention can be attached and used to detect the presence of the reagent based on the fluorescence of the energy transfer dye. Types of molecules and materials to which the dyes of the present invention may be attached to form a reagent include, but are not limited to, proteins, polypeptides, polysaccharides, nucleotides, nucleosides, oligonucleotides, oligonucleotide analogs (such as a peptide nucleic acid), lipids, solid supports, organic and inorganic polymers, and combinations and assemblages thereof, such as chromosomes, nuclei, living cells, such as bacteria, other microorganisms, mammalian cells, and tissues.

Preferred classes of reagents of the present invention are nucleotides, nucleosides, oligonucleotides and oligonucleotide analogs which have been modified to include an energy transfer dye of the invention. Examples of uses for nucleotide and nucleoside reagents include, but are not limited to, labeling oligonucleotides formed by enzymatic synthesis, e.g., nucleoside triphosphates used in the context of PCR amplification, Sanger-type nucleotide sequencing, and nick-translation reactions. Examples of uses for oligonucleotide reagents include, but are not limited to, as DNA sequencing primers, PCR primers, oligonucleotide hybridization probes, and the like.

One particular embodiment of the reagents are labeled nucleosides, such as cytosine, adenosine, guanosine, and thymidine, labeled with an energy transfer fluorescent dye of the present invention. These reagents may be used in a wide variety of methods involving oligonucleotide synthesis. Another related embodiment are labeled nucleotides (NTP), e.g., mono-, di- and triphosphate nucleoside phosphate esters. These reagents include, in particular, deoxynucleoside triphosphates (dNTP), such as deoxycytosine triphosphate, deoxyadenosine triphosphate, deoxyguanosine triphosphate, and deoxythymidine triphosphate, labeled with an energy transfer fluorescent dye of the present invention. These reagents may be used, for example, as polymerase substrates in the preparation of dye labeled oligonucleotides. These reagents also include labeled dideoxynucleoside triphosphates (ddNTP), such as dideoxycytosine triphosphate, dideoxyadenosine triphosphate, dideoxyguanosine triphosphate, and dideoxythymidine triphosphate, labeled with an energy transfer fluorescent dye of the present invention. These reagents may be used, for example, in dye termination sequencing.

Another embodiment of reagents are oligonucleotides which includes an energy transfer dye of the present invention. These reagents may be used, for example, in dye primer sequencing.

As used herein. "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g. as described in Kornberg and Baker, *DNA Replication*, 2nd Ed. (Freeman, San Francisco, 1992). The term "nucleotide" as used herein refers to a phosphate ester of a nucleoside, e.g., mono, di and triphosphate esters, wherein the most common site of esterification is the hydroxyl group attached to the C-5 position of the pentose. "Analogs" in reference to nucleosides include synthetic nucleosides having modified base moieties and/or modified sugar moieties, e.g. described generally by Scheit, *Nucleotide Analogs* (John Wiley, New York, 1980). The terms "labeled nucleoside" and "labeled nucleotide" refer to nucleosides and nucleotides which are covalently attached to an energy transfer dye through a linkage.

As used herein, the term "oligonucleotide" refers to linear polymers of natural or modified nucleoside monomers, including double and single stranded deoxyribonucleosides, ribonucleosides, α-anomeric forms thereof, and the like. Usually the nucleoside monomers are linked by phosphodiester linkages, where as used herein, the term "phosphodiester linkage" refers to phosphodiester bonds or analogs thereof including phosphorothioate, phosphorodithioate, phosphoroselenoate, phosphorodiselenoate, phosphoroanilothioate, phosphoranilidate, phosphoramidate, and the like, including associated counterions, e.g., H, $NH_4$, Na, and the like if such counterions are present. The oligonucleotides range in size form a few monomeric units, e.g. 8-40, to several thousands of monomeric units. Whenever an oligonucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted.

Nucleoside labeling can be accomplished using any of a large number of known nucleoside labeling techniques using known linkages, linking groups, and associated complementary functionalities. The linkage linking the dye and nucleoside should (i) be stable to oligonucleotide synthesis conditions, (ii) not interfere with oligonucleotide-target hybridization, (iii) be compatible with relevant enzymes, e.g., polymerases, ligases, and the like, and (iv) not quench the fluorescence of the dye.

Preferably, the dyes are covalently linked to the 5-carbon of pyrimidine bases and to the 7-carbon of 7-deazapurine bases. Several suitable base labeling procedures have been reported that can be used with the invention, e.g. Gibson et al, *Nucleic Acids Research*, 15 6455-6467 (1987); Gebeyehu et al, *Nucleic Acids Research*, 15 4513-4535 (1987); Haralambidis et al, *Nucleic Acids Research*, 15 4856-4876 (1987); Nelson et al., *Nucleosides and Nucleotides*, 5(3) 233-241 (1986); Bergstrom, et al., *JACS*, 111 374-375 (1989); U.S. Pat. Nos. 4,855,225, 5,231,191, and 5,449,767, each of which is incorporated herein by reference.

Preferably, the linkages are acetylenic amido or alkenic amido linkages, the linkage between the dye and the nucleotide base being formed by reacting an activated N-hydroxysuccinimide (NHS) ester of the dye with an alkynylamino-, alkynylethoxyamino- or alkenylamino-derivatized base of a nucleotide. More preferably, the resulting linkage is proargyl-1-ethoxyamido (3-(amino)ethoxy-1-propynyl), 3-(carboxy) amino-1-propynyl or 3-amino-1-propyn-1-yl.

Several preferred linkages for linking the dyes of the invention to a nucleoside base are shown below.

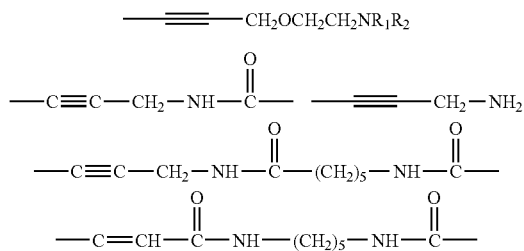

where $R_1$ and $R_2$ taken separately are H, alkyl, a protecting group or a fluorescent dye.

The synthesis of alkynylamino-derivatized nucleosides is taught by Hobbs et al. in European Patent Application No. 87305844.0, and Hobbs et al., *J. Org. Chem.*, 54 3420 (1989), which is incorporated herein by reference. Briefly, the alkynylamino-derivatized nucleotides are formed by placing the appropriate halodideoxynucleoside (usually 5-iodopyrimidine and 7-iodo-7-deazapurine dideoxynucleosides as taught by Hobbs et al. (cited above)) and Cu(I) in a flask, flushing with argon to remove air, adding dry DMF, followed by addition of an alkynylamine, triethyl-amine and Pd(0). The reaction mixture can be stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

The synthesis of oligonucleotides labeled with an energy transfer dye of the present invention can be accomplished using any of a large number of known oligonucleotide labeling techniques using known linkages, linking groups, and associated complementary functionalities. For example, labeled oligonucleotides may be synthesized enzymatically, e.g., using a DNA polymerase or ligase, e.g., Stryer, *Biochemistry*, Chapter 24, W.H. Freeman and Company (1981), or by chemical synthesis, e.g., by a phosphoramidite method, a phosphite-triester method, and the like, e.g., Gait, *Oligonucleotide Synthesis*, IRL Press (1990). Labels may be introduced during enzymatic synthesis utilizing labeled nucleoside triphosphate monomers, or introduced during chemical synthesis using labeled non-nucleotide or nucleotide phosphoramidites, or may be introduced subsequent to synthesis.

Generally, if the labeled oligonucleotide is made using enzymatic synthesis, the following procedure may be used. A template DNA is denatured and an oligonucleotide primer is annealed to the template DNA. A mixture of deoxynucleoside triphosphates is added to the reaction including dGTP, dATP, dCTP, and dTTP where at least a fraction of one of the deoxynucleotides is labeled with a dye compound of the invention as described above. Next, a polymerase enzyme is added under conditions where the polymerase enzyme is active. A labeled polynucleotide is formed by the incorporation of the labeled deoxynucleotides during polymerase strand synthesis. In an alternative enzymatic synthesis method, two primers are used instead of one, one primer complementary to the + strand and the other complementary to the − strand of the target, the polymerase is a thermostable polymerase, and the reaction temperature is cycled between a denaturation temperature and an extension temperature, thereby exponentially synthesizing a labeled complement to the target sequence by PCR, e.g., *PCR Protocols*, Innis et al. eds., Academic Press (1990).

Generally, if the labeled oligonucleotide is made using a chemical synthesis, it is preferred that a phosphoramidite method be used. Phosphoramidite compounds and the phosphoramidite method of polynucleotide synthesis are preferred in synthesizing oligonucleotides because of the efficient and rapid coupling and the stability of the starting materials. The synthesis is performed with the growing oligonucleotide chain attached to a solid support, so that excess reagents, which are in the liquid phase, can be easily removed by filtration, thereby eliminating the need for purification steps between cycles.

In view of the utility of phosphoramidite reagents in labeling nucleosides and oligonucleotides, the present invention also relates to phosphoramidite compounds which include an energy transfer dye of the present invention.

Nucleoside labeling with the dyes can be accomplished using any of a large number of known nucleoside labeling techniques using known linkages, linking groups, and associated complementary functionalities. Preferably, the dyes are covalently linked to the 5-carbon of pyrimidine bases and to the 7-carbon of 7-deazapurine bases. Several suitable base labeling procedures have been reported that can be used with the invention, e.g. Gibson et al. *Nucleic Acid Res.* 15 6455-6467 (1987); Gebeyehu et al. *Nucleic Acid Res.* 15 4513-4535 (1987); Haralambidis et al. Nucleic Acid Res. 15 4856-4876; Nelson et al. *Nucleosides and Nucleotides* 5 233-241 (1986); Bergstrom et al. *J. Am. Chem. Soc.* 111:374-375 (1989); U.S. Pat. Nos. 4,855,225, 5,231,191, and 5,449,767, each of which is incorporated herein by reference.

Preferably, the linkages are acetylenic amido or alkenic amido linkages, the linkage between the dye and nucleotide base being formed by reacting an activated N-hydroxysuccinimide (NHS) ester of the dye with an alkynylamino, alkynylethoxyamino, or alkenylamino-derivatized base of a nucelotide. More preferably, the resulting linkage is proargyl-1-ethoxyamido (3-(amino)ethoxy-1-propynyl), 3-(carboxy) amino-1-propynyl or 3-amino-1-propyn-1-yl.

The synthesis of alkynylamino-derivatized nucleosides is taught by Hobbs et al. *J. Org. Chem.* 54:3420 (1989), which is incorporated herein by reference. Briefly, the alkynylamino-derivatized nucleosides are formed by placing the appropriate halodideoxynucleoside (usually 5-iodopyrimidine and 7-iodo-deazapurine dideoxynucleosides as taught by Hobbs et al. as cited above) and Cu(I) in a flask, flushing with argon to remove air, adding dry DMF, followed by addition of an alkynylamine, triethyl-amine and Pd(0). The reaction mixture can be stirred for several hours, or until thin layer chromatography indicates consumption of the halo-dideoxynucleoside. When an unprotected alkynylamine is used, the alkynylaminonucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrate can be concentrated and purified by flash-chromatography on silica gel using a methanol-methylene chloride gradient. The triphosphates are obtained by standard techniques.

Detailed descriptions of the chemistry used to form oligonucleotides by the phosphoramidite method are provided in Caruthers et al., U.S. Pat. No. 4,458,066; Caruthers et al., U.S. Pat. No. 4,415,732; Caruthers et al., *Genetic Engineering*, 4 1-17 (1982); *Users Manual Model* 392 and 394 *Polynucleotide Synthesizers*, pages 6-1 through 6-22, Applied Biosystems, Part No. 901237 (1991), each of which are incorporated by reference in their entirety.

The following briefly describes the steps of a typical oligonucleotide synthesis cycle using the phosphoramidite method. First, a solid support including a protected nucleotide monomer is treated with acid, e.g., trichloroacetic acid, to remove a 5'-hydroxyl protecting group, freeing the hydroxyl for a subsequent coupling reaction. An activated intermediate is then formed by simultaneously adding a protected phosphoramidite nucleoside monomer and a weak acid, e.g., tetrazole, to the reaction. The weak acid protonates the nitrogen of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and the hydroxyl protecting groups on the dyes are removed by treating the polynucleotide solution in base at an elevated temperature, e.g., 55° C.

Any of the phosphoramidite nucleoside monomers may be dye-labeled phosphoramidites. If the 5'-terminal position of the nucleotide is labeled, a labeled non-nucleotidic phosphoramidite of the invention may be used during the final condensation step. If an internal position of the oligonucleotide is to be labeled, a labeled nucleotidic phosphoramidite of the invention may be used during any of the condensation steps. Subsequent to their synthesis, oligonucleotides may be labeled at a number of positions including the 5'-terminus. See *Oligonucleotides and Analogs*, Eckstein ed., Chapter 8, IRL Press (1991) and Orgel et al., *Nucleic Acids Research* 11(18) 6513 (1983); U.S. Pat. No. 5,118,800, each of which are incorporated by reference.

Oligonucleotides may also be labeled on their phosphodiester backbone (*Oligonucleotides and Analogs*, Eckstein ed., Chapter 9) or at the 3'-terminus (Nelson, *Nucleic Acids Research* 20(23) 6253-6259, and U.S. Pat. Nos. 5,401,837 and 5,141,813, both patents hereby incorporated by reference. For a review of oligonucleotide labeling procedures see R. Haugland in *Excited States of Biopolymers*, Steiner ed., Plenum Press, NY (1983).

In one preferred post-synthesis chemical labeling method an oligonucleotide is labeled as follows. A dye including a carboxy linking group is converted to the n-hydroxysuccinimide ester by reacting with approximately 1 equivalent of 1,3-dicyclohexylcarbodiimide and approximately 3 equivalents of n-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10-20×) to an aminohexyl derivatized oligonucleotide in 0.25 M bicarbonate/carbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g., 0.1 molar triethylamine acetate (TEM). The fraction containing the crude labeled oligonucleotide is further purified by reverse phase HPLC employing gradient elution.

III. Methods Employing Dyes And Reagents Of The Present Invention

The energy transfer dyes and reagents of the present invention may be used in a wide variety of methods for detecting the presence of a component in a sample by labeling the component in the sample with a reagent containing the dye. In particular, the energy transfer dyes and reagents of the present invention are well suited for use in methods which combine separation and fluorescent detection techniques, particularly methods requiring the simultaneous detection of multiple spatially-overlapping analytes. For example, the dyes and reagents are particularly well suited for identifying classes of oligonucleotides that have been subjected to a biochemical separation procedure, such as electrophoresis, where a series of bands or spots of target substances having similar physiochemical properties, e.g. size, conformation, charge, hydrophobicity, or the like, are present in a linear or planar arrangement. As used herein, the term "bands" includes any spatial grouping or aggregation of analytes on the basis of similar or identical physiochemical properties. Usually bands arise in the separation of dye-oligonucleotide conjugates by electrophoresis.

Classes of oligonucleotides can arise in a variety of contexts. In a preferred category of methods referred to herein as "fragment analysis" or "genetic analysis" methods, labeled oligonucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography; and, the separated fragments are detected subsequent to the separation, e.g., by laser-induced fluorescence. In a particularly preferred embodiment, multiple classes of oligonucleotides are separated simultaneously and the different classes are distinguished by spectrally resolvable labels.

One such fragment analysis method is amplified fragment length polymorphisim detection (AmpFLP) and is based on amplified fragment length polymorphisms, i.e., restriction fragment length polymorphisms that are amplified by PCR. These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled oligonucleotide PCR primer, or by utilizing labeled nucleotide triphosphates in the PCR.

Another fragment analysis method is nick translation. Nick translation involves a reaction to replace unlabeled nucleotide triphosphates in a double-stranded DNA molecule with labeled ones. Free 3'-hydroxyl groups are created within the unlabeled DNA by "nicks" caused by deoxyribonuclease I (DNAase I) treatment. DNA polymerase I then catalyzes the addition of a labeled nucleotide to the 3'-hydroxyl terminus of the nick. At the same time, the 5' to 3'-exonuclease activity of this enzyme eliminates the nucleotide unit from the 5'-phosphoryl terminus of the nick. A new nucleotide with a free 3'-OH group is incorporated at the position of the original excised nucleotide, and the nick is shifted along by one nucleotide unit in the 3' direction. This 3' shift will result in the sequential addition of new labeled nucleotides to the DNA with the removal of existing unlabeled nucleotides. The nick-translated polynucleotide is then analyzed using a separation process, e.g., electrophoresis.

Another exemplary fragment analysis method is based on variable number of tandem repeats, or VNTRs. VNTRs are regions of double-stranded DNA that contain adjacent multiple copies of a particular sequence with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2-4 bases) repeated sequence. One of the most abundant interspersed repetitive DNA families in humans is the (dC-dA)n-(dG-dT)n dinucleotide repeat family (also called the (CA)n dinucleotide repeat family). There are thought to be as many as 50,000 to 100,000 (CA)n repeat regions in the human genome, typically with 15-30 repeats per block. Many of these repeat regions are polymorphic in length and can therefore serve as useful genetic markers. Preferably, in VNTR or STR methods, label is introduced into the polynucleotide fragments by using a dye-labeled PCR primer.

Another exemplary fragment analysis method is DNA sequencing. In general, DNA sequencing involves an extension/termination reaction of an oligonucleotide primer. Included in the reaction mixture are deoxynucleoside triphosphates (dNTPs) which are used to extend the primer. Also included in the reaction mixture is at least one dideoxynucleoside triphosphate (ddNTP) which when incorporated onto the extended primer prevents the further extension of the primer. After the extension reaction has been terminated, the different termination products that are formed are separated and analyzed in order to determine the positioning of the different nucleosides.

Fluorescent DNA sequencing may generally be divided into two categories, "dye primer sequencing" and "dye terminator sequencing". In dye primer sequencing, a fluorescent dye is incorporated onto the primer being extended. Four separate extension/termination reactions are then run in parallel, each extension reaction containing a different dideoxynucleoside triphosphate (ddNTP) to terminate the extension reaction. After termination, the reaction products are separated by gel electrophoresis and analyzed. See, for example, Ansorge et al., *Nucleic Acids Res.* 15 4593-4602 (1987).

In one variation of dye primer sequencing, different primers are used in the four separate extension/termination reactions, each primer containing a different spectrally resolvable dye. After termination, the reaction products from the four extension/termination reactions are pooled, electrophoretically separated, and detected in a single lane. See, for example, Smith et al., *Nature* 321 674-679 (1986). Thus, in this variation of dye primer sequencing, by using primers containing a set of spectrally resolvable dyes, products from more than one extension/termination reactions can be simultaneously detected.

In dye terminator sequencing, a fluorescent dye is attached to each of the dideoxynucleoside triphosphates. An extension/termination reaction is then conducted where a primer is extended using deoxynucleoside triphosphates until the labeled dideoxynucleoside triphosphate is incorporated into the extended primer to prevent further extension of the primer. Once terminated, the reaction products for each dideoxynucleoside triphosphate are separated and detected. In one embodiment, separate extension/termination reactions are conducted for each of the four dideoxynucleoside triphosphates. In another embodiment, a single extension/termination reaction is conducted which contains the four dideoxynucleoside triphosphates, each labeled with a different, spectrally resolvable fluorescent dye.

Thus according to one aspect of the invention, a method is provided for conducting dye primer sequencing using one or more oligonucleotide reagents of the present invention. According to this method, a mixture of extended labeled primers are formed by hybridizing a nucleic acid sequence with a fluorescently labeled oligonucleotide primer in the presence of deoxynucleoside triphosphates, at least one dideoxynucleoside triphosphate and a DNA polymerase. The fluorescently labeled oligonucleotide primer includes an oligonucleotide sequence complementary to a portion of the nucleic acid sequence being sequenced, and an energy transfer fluorescent dye attached to the oligonucleotide.

According to the method, the DNA polymerase extends the primer with the deoxynucleoside triphosphates until a dideoxynucleoside triphosphate is incorporated which terminates extension of the primer. After termination, the mixture of extended primers are separated. The sequence of the nucleic acid sequence is then determined by fluorescently detecting the mixture of extended primers formed.

In a further embodiment of this method, four dye primer sequencing reactions are run, each primer sequencing reaction including a different fluorescently labeled oligonucleotide primer and a different dideoxynucleoside triphosphate (ddATP, ddCTP, ddGTP and ddTTP). After the four dye primer sequencing reactions are run, the resulting mixtures of extended primers may be pooled. The mixture of extended primers may then be separated, for example by electrophoresis and the fluorescent signal from each of the four different fluorescently labeled oligonucleotide primers detected in order to determine the sequence of the nucleic acid sequence.

According to a further aspect of the invention, a method is provided for conducting dye terminator sequencing using one or more dideoxynucleoside triphosphates labeled with an energy transfer dye of the present invention. According to this method, a mixture of extended primers are formed by hybridizing a nucleic acid sequence with an oligonucleotide primer in the presence of deoxynucleoside triphosphates, at least one fluorescently labeled dideoxynucleotide triphosphate and a DNA polymerase. The fluorescently labeled dideoxynucleotide triphosphate includes a dideoxynucleoside triphosphate labeled with an energy transfer fluorescent dye of the present invention.

According to this method, the DNA polymerase extends the primer with the deoxynucleoside triphosphates until a fluorescently labeled dideoxynucleoside triphosphate is incorporated into the extended primer. After termination, the mixture of extended primers are separated. The sequence of the nucleic acid sequence is then determined by detecting the fluorescently labeled dideoxynucleoside attached to the extended primer.

In a further embodiment of this method, the step of forming a mixture of extended primers includes hybridizing the nucleic acid sequence with four different fluorescently labeled dideoxynucleoside triphosphates, i.e., a fluorescently labeled dideoxycytosine triphosphate, a fluorescently labeled dideoxyadenosine triphosphate, a fluorescently labeled dideoxyguanosine triphosphate, and a fluorescently labeled dideoxythymidine triphosphate.

In each of the above-described fragment analysis methods, the labeled oligonucleotides are preferably separated by electrophoretic procedures, e.g. Gould and Matthews, cited above; Rickwood and Hames, Eds., *Gel Electrophoresis of Nucleic Acids: A Practical Approach*, (IRL Press Limited, London, 1981); or Osterman, *Methods of Protein and Nucleic Acid Research*, Vol. 1 Springer-Verlag, Berlin, 1984). Preferably the type of electrophoretic matrix is crosslinked or uncrosslinked polyacrylamide having a concentration (weight to volume) of between about 2-20 weight percent. More preferably, the polyacrylamide concentration is between about 4-8 percent. Preferably in the context of DNA sequencing in particular, the electrophoresis matrix includes a strand separating, or denaturing, agent, e.g., urea, formamide, and the like. Detailed procedures for constructing such matrices are given by Maniatis et al., "Fractionation of Low Molecular Weight DNA and RNA in Polyacrylamide Gels Containing 98% Formamide or 7M Urea," in *Methods in Enzymology*, 65 299-305 (1980); Maniatis et al., "Chain Length Determination of Small Double- and Single-Stranded DNA Molecules by Polyacrylamide Gel Electrophoresis," *Biochemistry*, 14 3787-3794 (1975); Maniatis et al., *Molecular Cloning: A Laboratory Manual* (Cold Spring Harbor Laboratory, New York, 1982), pgs. 179-185; and ABI PRISM™ 377 *DNA Sequencer User's Manual, Rev.* A, January 1995, Chapter 2 (p/n 903433, The Perkin-Elmer Corporation, Foster City, Calif.), each of which are incorporated by reference. The optimal polymer concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. By way of example, oligonucleotides having sizes in the range of between about 20-300 bases have been separated and detected in accordance with the invention in the following matrix: 6 percent polyacrylamide made from 19 parts to 1 part acrylamide to bis-acrylamide, formed in a Tris-borate EDTA buffer at pH 8.3.

After electrophoretic separation, the dye-oligonucleotide conjugates are detected by measuring the fluorescence emission from the dye labeled polynucleotides. To perform such detection, the labeled polynucleotides are illuminated by standard light sources, e.g. high intensity mercury vapor lamps, lasers, or the like. Previously, fluorescein and rhodamine—based dyes and fluorescein-linked energy transfer dyes have been used which are excited at a wavelength between 488 and 550 nm. However, the donor dyes used in the energy transfer dyes of the present invention typically have absorption maxima below 450 nm and thus may be excited at shorter wavelengths, preferably between 250 and 450 nm.

IV. Detection Methods Using Shorter Wavelength Light Sources

The present invention also relates to detection methods, such as the detection methods described above in Section III, in which a shorter wavelength light source is used, preferably a light source emitting light between 250 and 450 nm. As noted above, several of the energy transfer dyes of the present invention have the feature of having a donor dye with an emission maxima between about 250 and 450 nm and an acceptor dye which has an emission maxima at a wavelength greater than about 500 nm. As a result, these dyes enable these shorter wavelength light sources to be used. Accordingly, the present invention relates to methods for using these shorter wavelength light sources. It is noted that the use of these shorter wavelength light sources in detection methods, such as the ones described in Section III, is not intended to be limited to the energy transfer dyes of the present invention but rather are intended to encompass the use of any energy transfer dye which can be excited using light having a wavelength between 250 and 450 nm V. Kits Incorporating The Energy Transfer Dyes The present invention also relates to kits having combinations of energy transfer dyes and/or reagents. In one embodiment, the kit includes at least two spectrally resolvable energy transfer dyes according to the present invention. In this kit, the energy transfer dyes preferably include the same donor dye so that a single light source is needed to excite the dyes.

In another embodiment, the kit includes dideoxycytosine triphosphate, dideoxyadenosine triphosphate, dideoxyguanosine triphosphate, and dideoxythymidine triphosphate, each dideoxynucleotide triphosphate labeled with an energy transfer dye according to the present invention. In one embodiment, each energy transfer dye is spectrally resolvable from the other energy transfer dyes attached to the other dideoxynucleotide triphosphates. In this kit, the energy transfer dyes preferably include the same first xanthene dye.

In yet another embodiment, the kit includes at least two oligonucleotides, each oligonucleotide including an energy transfer dye according to the present invention. In one embodiment, each oligonucleotide contains an energy transfer dye which is spectrally resolvable from the energy transfer dyes attached to the other oligonucleotides. In another embodiment, the kit includes at least four oligonucleotides which each contain a spectrally resolvable energy transfer dye.

The energy transfer dyes and their use in DNA sequencing is illustrated by the following examples. Further objectives and advantages other than those set forth above become apparent from the examples.

EXAMPLES

1. Method of Synthesis of DYE104

A solution of 5CF-B (8 mg in 0.45 mL dimethylformamide (DMF), 20 µL) was added to a solution of the succimidyl ester of coumarin DYE114 (20 µL of a 5 mg/200 µL DMF solution). Diisopropylethylamine (5 µL) was added. After 5 min, 200 µL of 5% HCl was added. The mixture was centrifuged.

Figure 9:
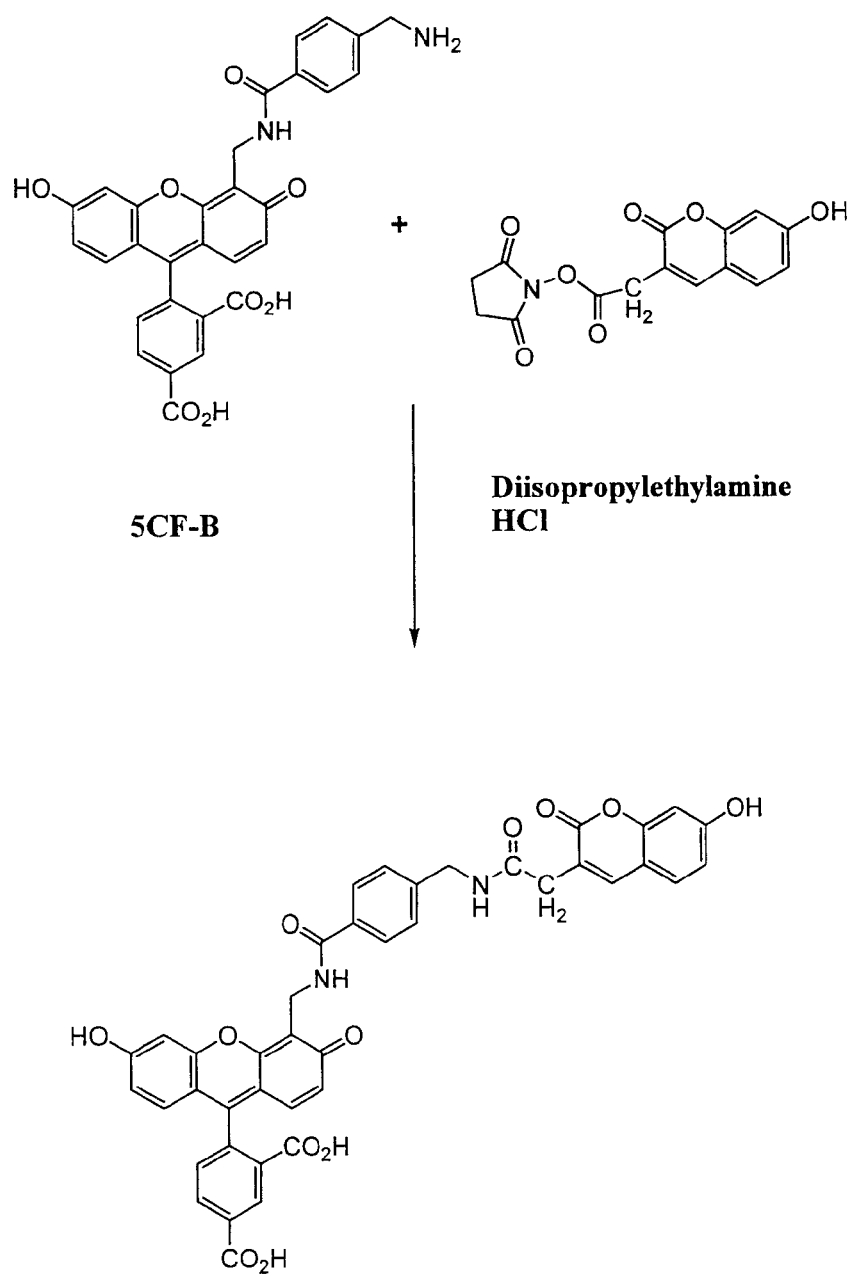
FIG. 9 illustrates the synthesis scheme of energy transfer dye DYE104.

The solid was dissolved in bicarbonate solution and purified by reverse-phase HPLC. The synthesis scheme of DYE104 is illustrated in FIG. 9.

2. Method of Synthesis of DYE106

Figure 10:
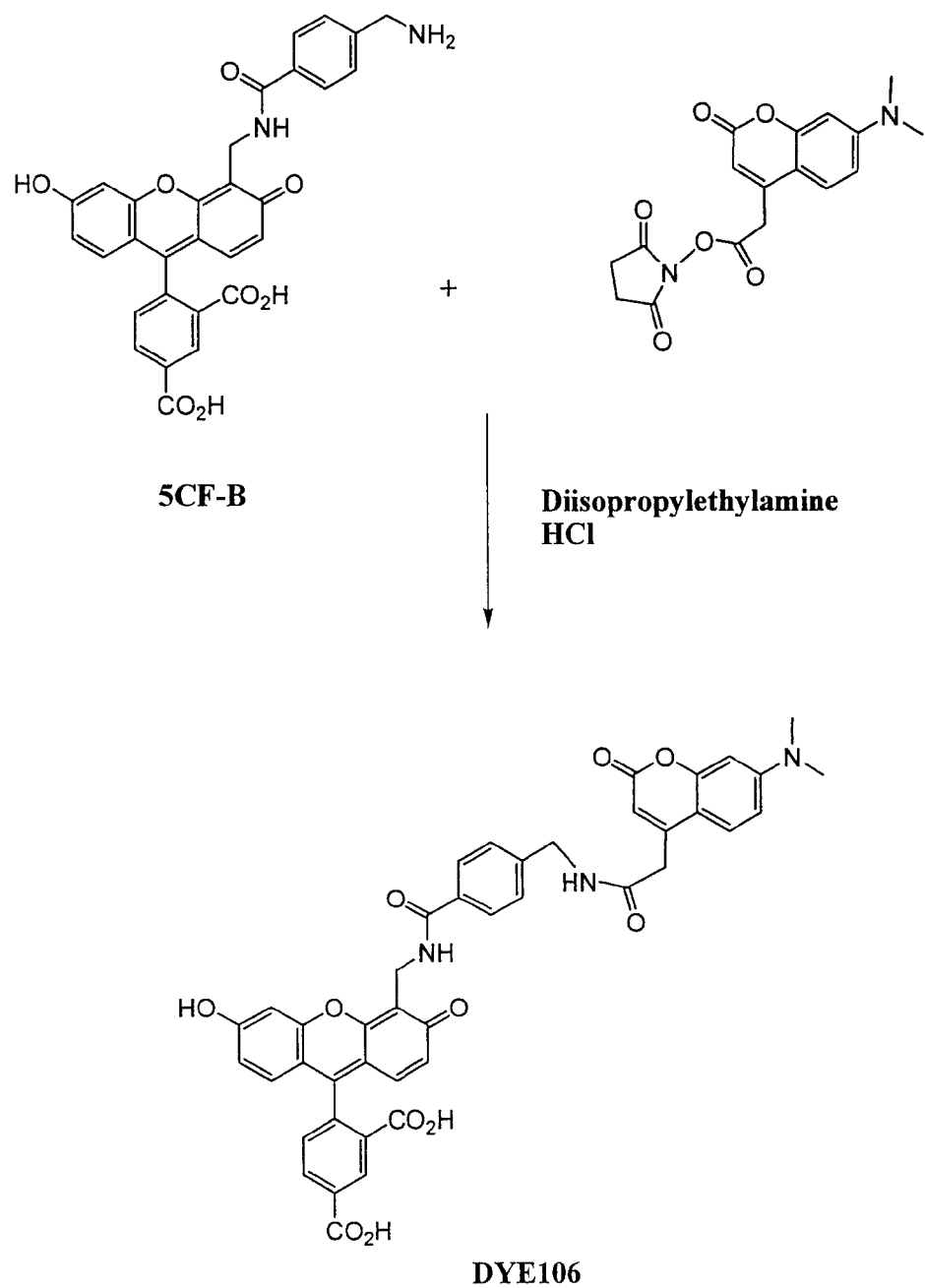
FIG. 10 illustrates the synthesis scheme of energy transfer dye DYE106.

A solution of 5CF-B (8 mg in 0.45 mL dimethylformamide (DMF), 20 µL) was added to a solution of the succinimidyl ester of coumarin DYE116 (20 µL of a 5 mg/200 µL DMF solution). Diisopropylethyiamine (5 µL) was added. After 5 min, 200 µL of 5% HCl was added. The mixture was centrifuged. The solid was dissolved in bicarbonate solution and purified by reverse-phase HPLC. The synthesis scheme of DYE106 is illustrated in FIG. 10.

2. Method of Synthesis of DYE108

Figure 11:
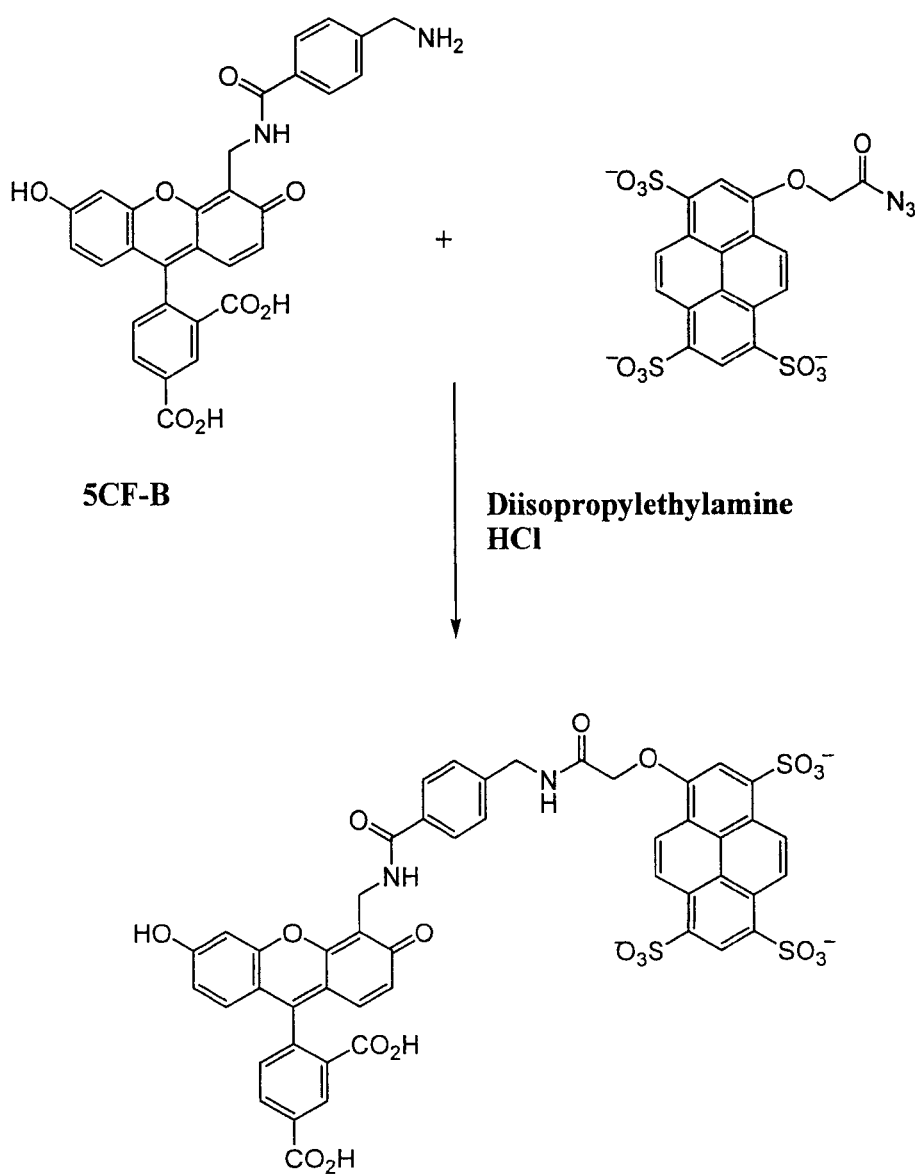
FIG. 11 illustrates the synthesis scheme of energy transfer dye DYE108.

A solution of 5CF-B (8 mg in 0.45 mL dimethylformamide (DMF), 20 µL) was added to a solution (20 µL of a 5 mg/200 µL DMF solution) of DYE110, trisulfopyrene acetyl azide (or Cascade Blue acetyl azide, Molecular Probes). Diisopropylethylamine (5 µL) was added. After 5 min, 200 µL of 5% HCl was added. The mixture was centrifuged. The solid was dissolved in bicarbonate solution and purified by reverse-phase HPLC. The synthesis scheme of DYE108 is illustrated in FIG. 11.

3. Comparison of Fluorescence Emission Spectra of 5CF-B-Conjugates

The following example compares the fluorescence emission spectra of a series of energy transfer dyes according to the present invention. Dye solutions of 5CF-B, DYE102, DYE104, DYE106, and DYE108 were measured in Tris-EDTA.

Figure 12:
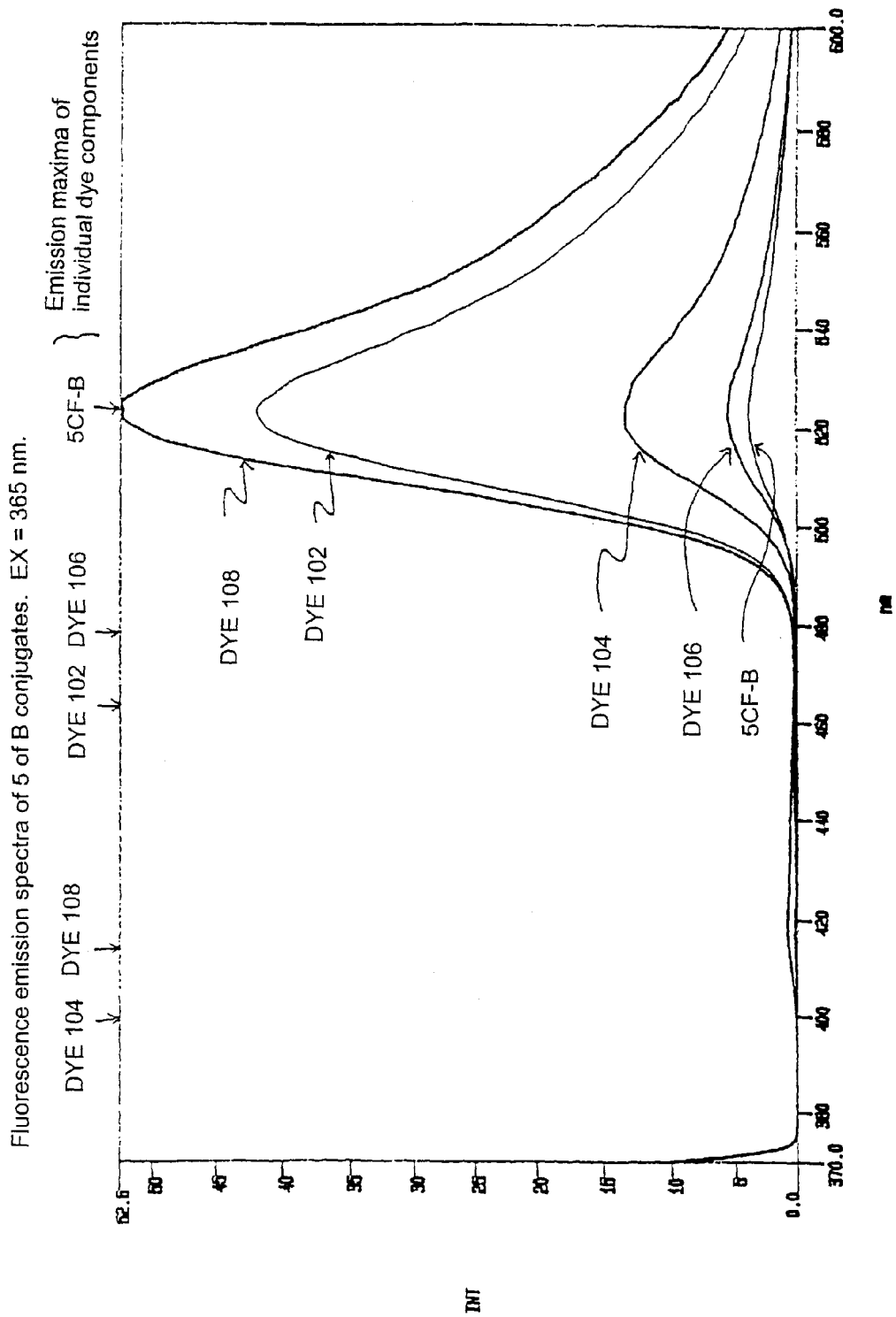
FIG. 12 shows the fluorescence emission spectra of energy transfer dyes according to the present invention.

The structures of these dyes are illustrated in FIG. 1. FIG. 12 provides a graph of the relative fluorescence emission of each of these dyes when excited at 365 nm. FIG. 12 also show the emission maxima of the individual dye components. As shown in FIG. 12, the emissions of the donor dyes do not overlap with the absorbance of the acceptor dye. The best conjugate, DYE108, is more than 10-fold brighter than 5CF-B alone.

Table 1 shows the relative spectral data and relative quantum yields of 5CF-B conjugates. As can be seen from Table 1, the quantum yields are high and the energy transfer is practically quantitative, as observed by the lack of emission of the donor dyes. Coumarin based dyes DYE104 and DYE102 and pyrene based dye DYE108 display high quantum yields indicating that the acceptor is able to absorb substantially all of the energy emitted by the donor dye. In contrast, the DYE106 (coumarin) displays poor quantum yield and inefficient energy transfer.

TABLE 1

| 5CF-B conjugate | EX/EM Maxima of Individual Dyes (nm) | Quantum Yield of Conjugate Relative to 5CF-B |
|---|---|---|
| 5CF-B | 495/523 | 1.00 |
| DYE106 | 376/468 | 0.17 |
| DYE104 | 328/386 | 0.93 |
| DYE108 | 396/410 | 0.91 |
| DYE102 | 362/459 | 0.87 |

4. Method of Synthesis of Pyrenetrisulfonate-Rhodamine Dye (DYE120)

D-Rox succinimidyl ester (3 mg), 1,4-cyclohexanediamine (7 mg), DMF (100 µL) and diisopropylethylamine (10 µL) were combined. After 5 min ethyl ether was added. The mixture was centrifuged and decanted. The residue was dissolved in methanol and an aliquot was purified by reverse-phase HPLC to separate the d-Rox-acid from the d-Rox-cyclohexanediamine adduct. The purified adduct was concentrated to dryness and dissolved in 10 µL DMF.

Figure 13:
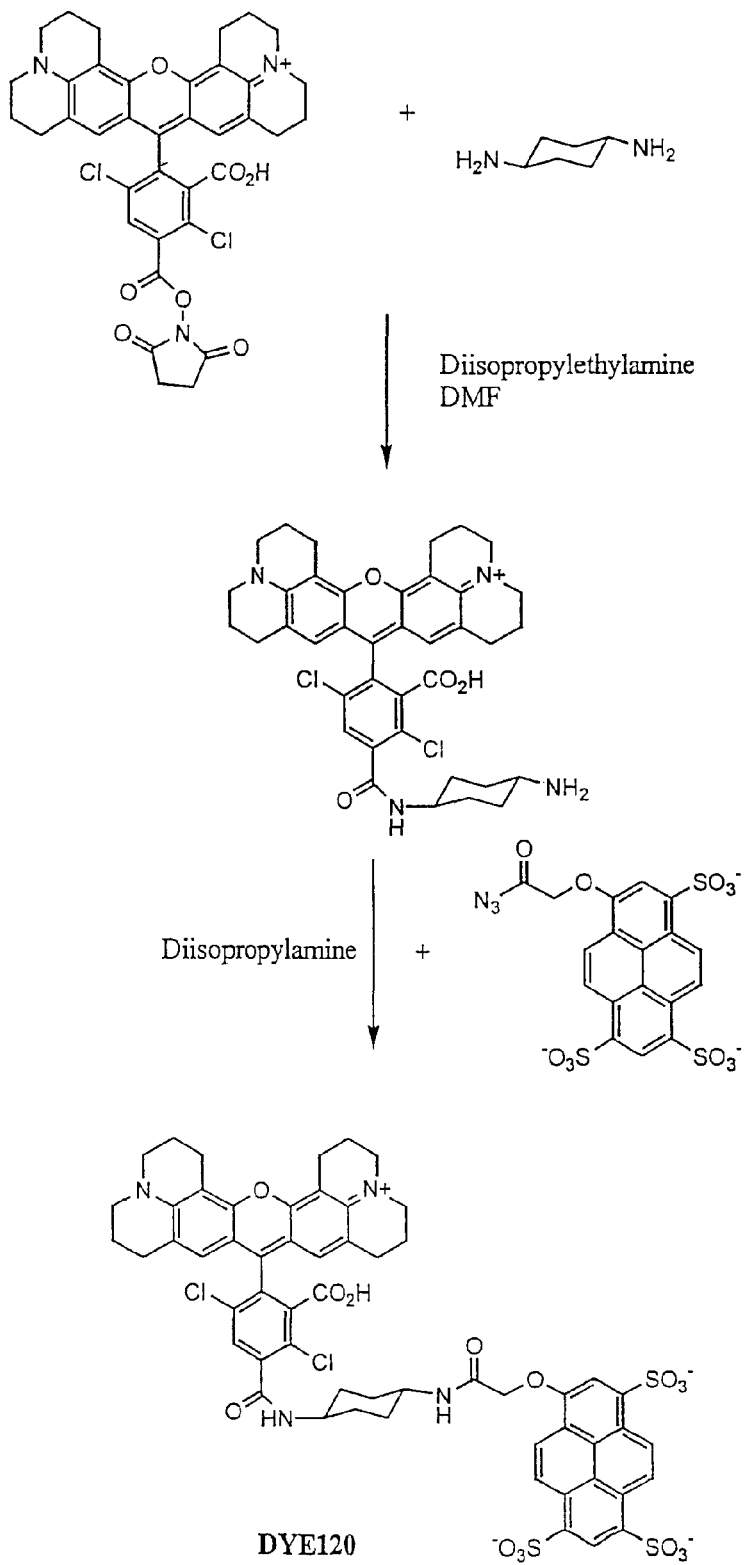
FIG. 13 illustrates the synthesis scheme of energy transfer dye DYE120.

A solution of DYE110, Cascade Blue acetyl azide, was made (Molecular Probes, 8 mg/100 µL DMF). To 5 µL of the Dye110 solution was added the d-Rox-cyclohexanediamine adduct and 2 µL diisopropylamine. The mixture was purified by reverse-phase HPLC. The synthesis scheme of pyrenetrisulfonate-d-Rox dye (DYE120) is illustrated in FIG. 13.

Figure 14:
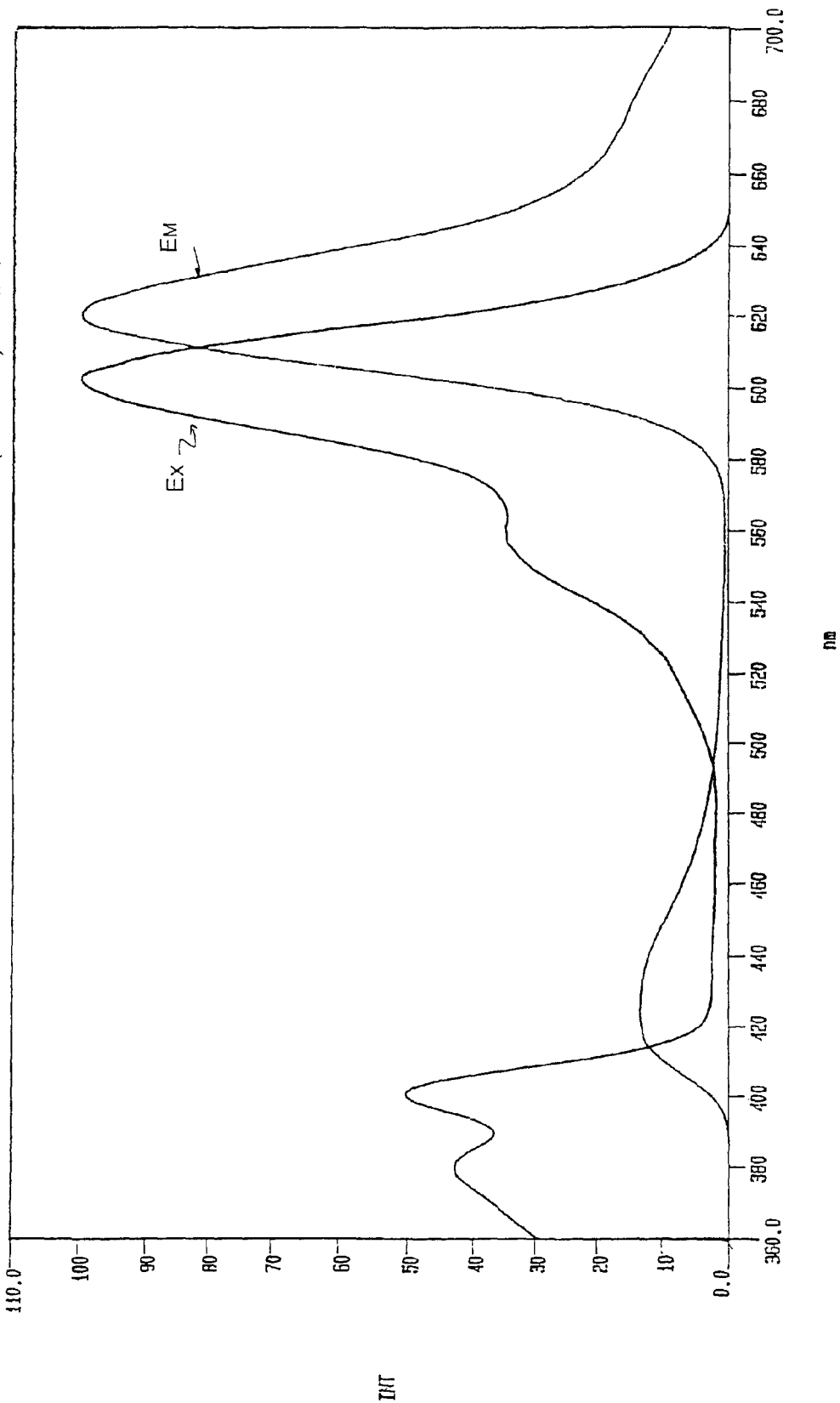
FIG. 14 shows the fluorescence emission spectra of energy transfer dye DYE120 according to the present invention.

Normalized excitation and emission spectra of the pyrenetrisulfonate-d-Rox adduct (DYE120) are shown in FIG. 14. Very little pyrenetrisulfonate emission (410 nm) was observed. The excitation spectra showed a peak at 400 nm that was 50% of the maximum peak at 600 nm.

While the present invention is disclosed by reference to the preferred embodiments and examples detailed above, it is to be understood that these examples are intended in an illustrative rather than limiting sense. As it is contemplated that modifications will readily occur to those skilled in the art, which modifications will be within the spirit of the invention and the scope of the appended claims. With regard to all of the molecular structures provided herein, it is intended that these molecular structures encompass not only the exact electronic structure presented, but also include all resonant structures and protonation states thereof.

What is claimed is:

1. An energy transfer dye comprising:
    a donor dye having an absorption maxima at a wavelength between about 250 to 450 nm; and
    a acceptor dye capable of absorbing excitation energy emitted by the donor dye and emitting light in response, the acceptor dye having an emission maxima greater than about 500 nm.

* * * * *